(12) United States Patent
Morita et al.

(10) Patent No.: US 6,985,765 B2
(45) Date of Patent: Jan. 10, 2006

(54) THREE-DIMENSIONAL OBSERVATION APPARATUS AND METHOD OF THREE-DIMENSIONAL OBSERVATION

(75) Inventors: Kazuo Morita, Hachioji (JP); Susumu Takahashi, Iruma (JP); Masahiro Kudo, Hino (JP); Nobuaki Akui, Hino (JP); Hiroyuki Kuroda, Hachioji (JP); Kazuo Banju, Hachioji (JP); Shingo Nogami, Kanagawa (JP); Takahiro Kogasaka, Hino (JP); Takechiyo Nakamitsu, Hachioji (JP); Takeaki Nakamura, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 10/359,393

(22) Filed: Feb. 6, 2003

(65) Prior Publication Data

US 2003/0218720 A1    Nov. 27, 2003

(30) Foreign Application Priority Data

Feb. 7, 2002    (JP)    ............................. 2002-031426

(51) Int. Cl.
A61B 5/05    (2006.01)

(52) U.S. Cl. .................................... 600/407
(58) Field of Classification Search ................ 359/630, 359/631, 633, 619, 449, 462, 463, 464, 466, 359/376, 377, 378; 351/201, 211, 220, 237, 351/240, 243, 246; 600/407–447; 128/916
See application file for complete search history.

(56) References Cited

U.S. PATENT DOCUMENTS

| | | | | |
|---|---|---|---|---|
| 5,186,174 A | * | 2/1993 | Schlondorff et al. | 600/426 |
| 5,279,309 A | * | 1/1994 | Taylor et al. | 600/595 |
| 5,417,210 A | * | 5/1995 | Funda et al. | 600/425 |
| 5,614,941 A | | 3/1997 | Hines | 348/42 |
| 5,712,732 A | | 1/1998 | Street | 359/630 |
| 6,122,541 A | * | 9/2000 | Cosman et al. | 600/426 |
| 6,226,548 B1 | * | 5/2001 | Foley et al. | 600/426 |
| 6,409,722 B1 | * | 6/2002 | Hoey et al. | 606/34 |
| 6,484,049 B1 | * | 11/2002 | Seeley et al. | 600/426 |
| 6,602,185 B1 | * | 8/2003 | Uchikubo | 600/118 |
| 6,827,723 B2 | * | 12/2004 | Carson | 606/130 |
| 2002/0186348 A1 | * | 12/2002 | Covannon et al. | 351/240 |
| 2003/0069588 A1 | * | 4/2003 | Vilsmeier et al. | 606/116 |
| 2003/0133191 A1 | * | 7/2003 | Morita et al. | 359/464 |

FOREIGN PATENT DOCUMENTS

| | | | |
|---|---|---|---|
| JP | 51-24116 | | 2/1976 |
| JP | 2002-007780 | * | 1/2002 |

* cited by examiner

Primary Examiner—Francis J. Jaworski
(74) Attorney, Agent, or Firm—Scully, Scott, Murphy & Presser

(57) ABSTRACT

A three-dimensional observation apparatus is provided which includes an optical reflection member which reflects a light beam and converges the light beam after the reflection, and image projectors for right and left eyes which project a medical image for the right and left eyes on the optical reflection member and forms an exit pupil for the right and left eyes at a position apart from the optical reflection member by a predetermined distance. The apparatus also includes a holding member which keeps a positional relationship of the image projector for the right eye to the optical reflection member and a positional relationship of the image projector for the left eye to the optical reflection member.

6 Claims, 23 Drawing Sheets

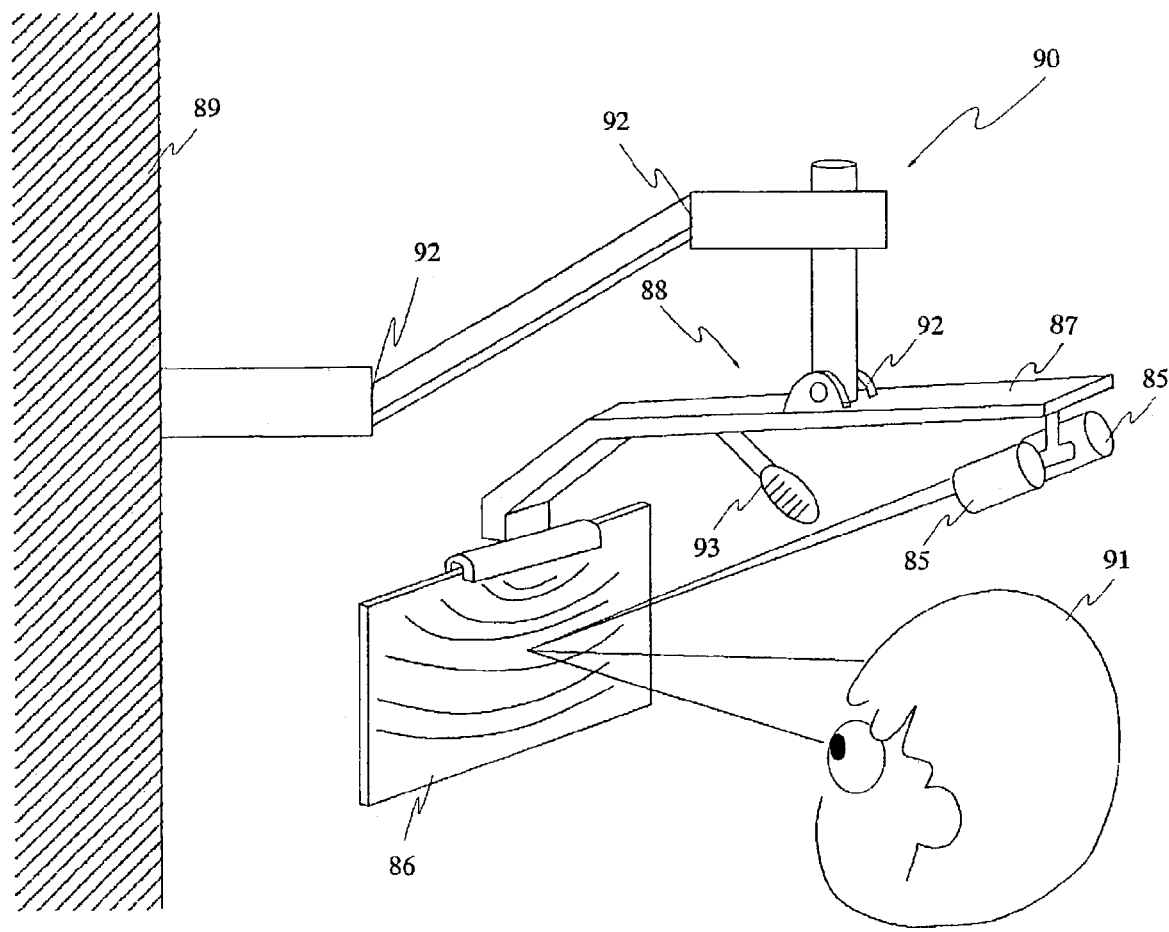
F I G. 1 0

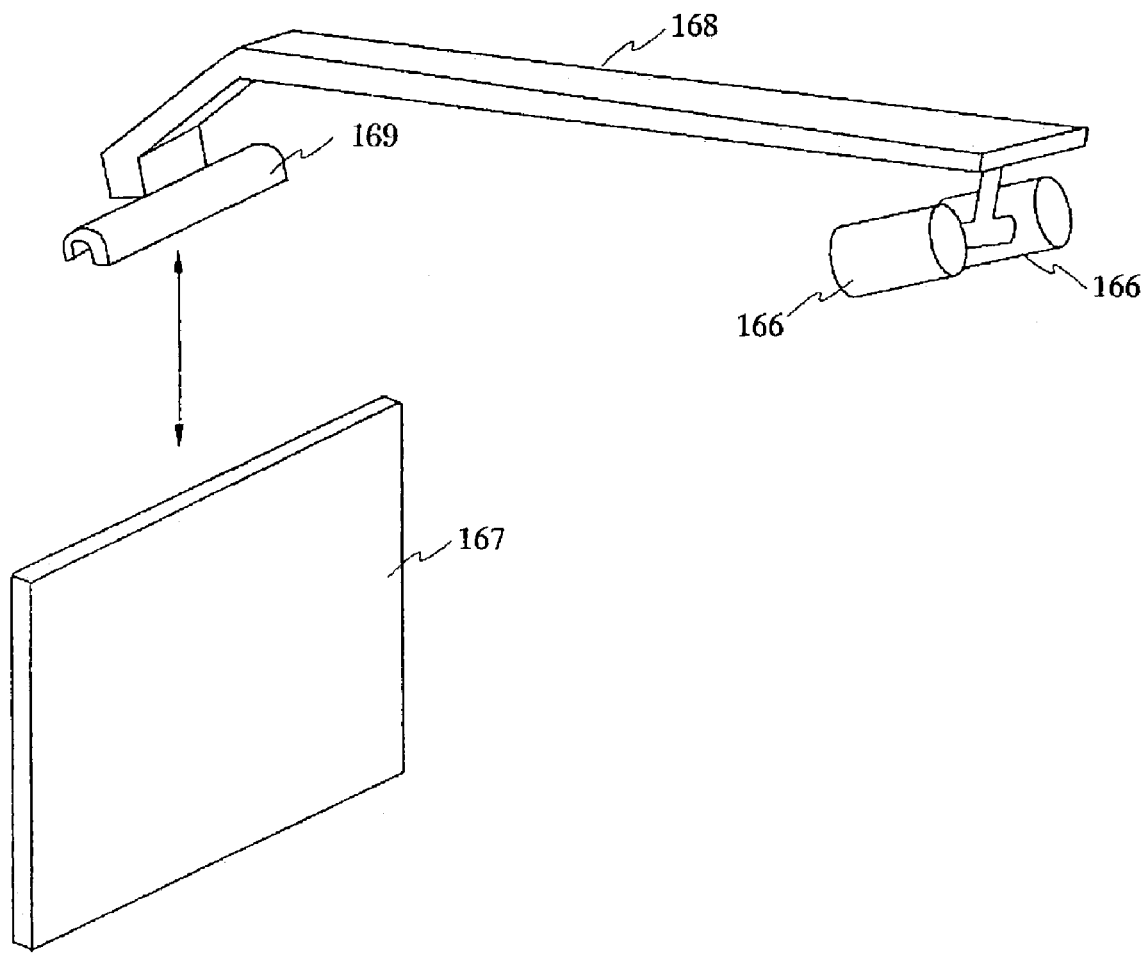
F I G. 2 0

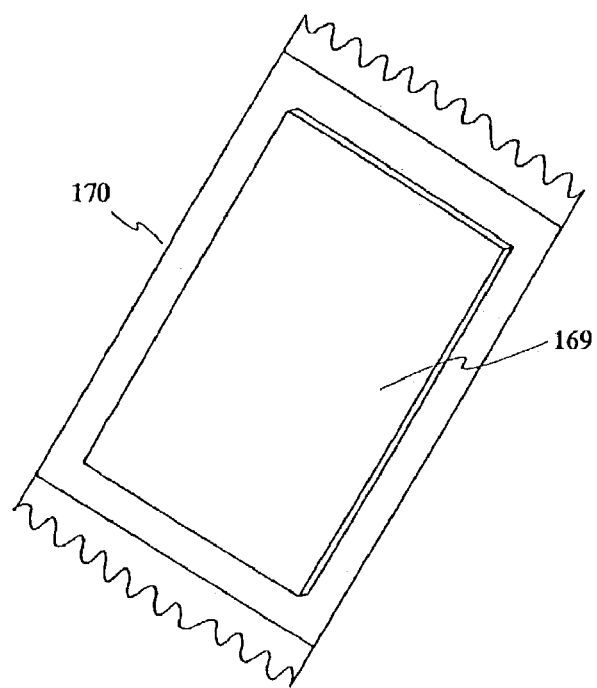
F I G. 2 1
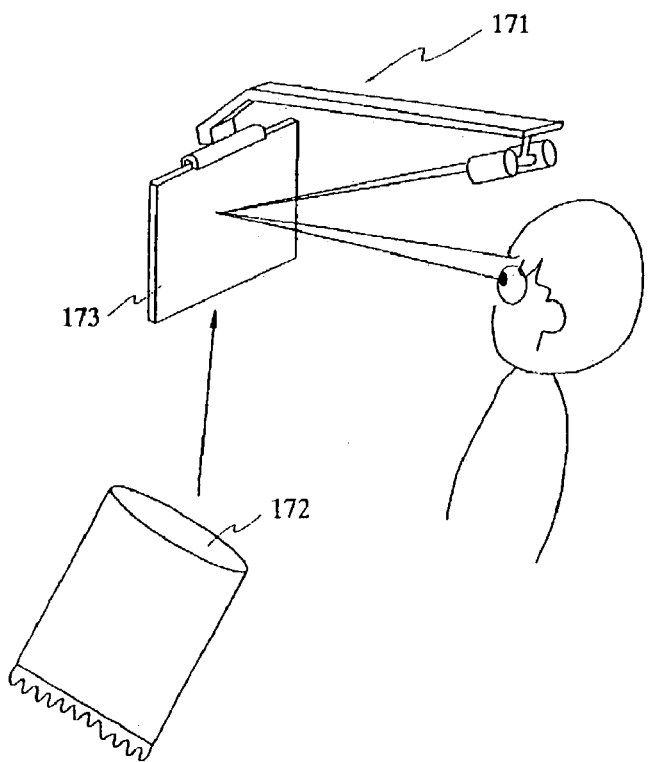
F I G. 2 2

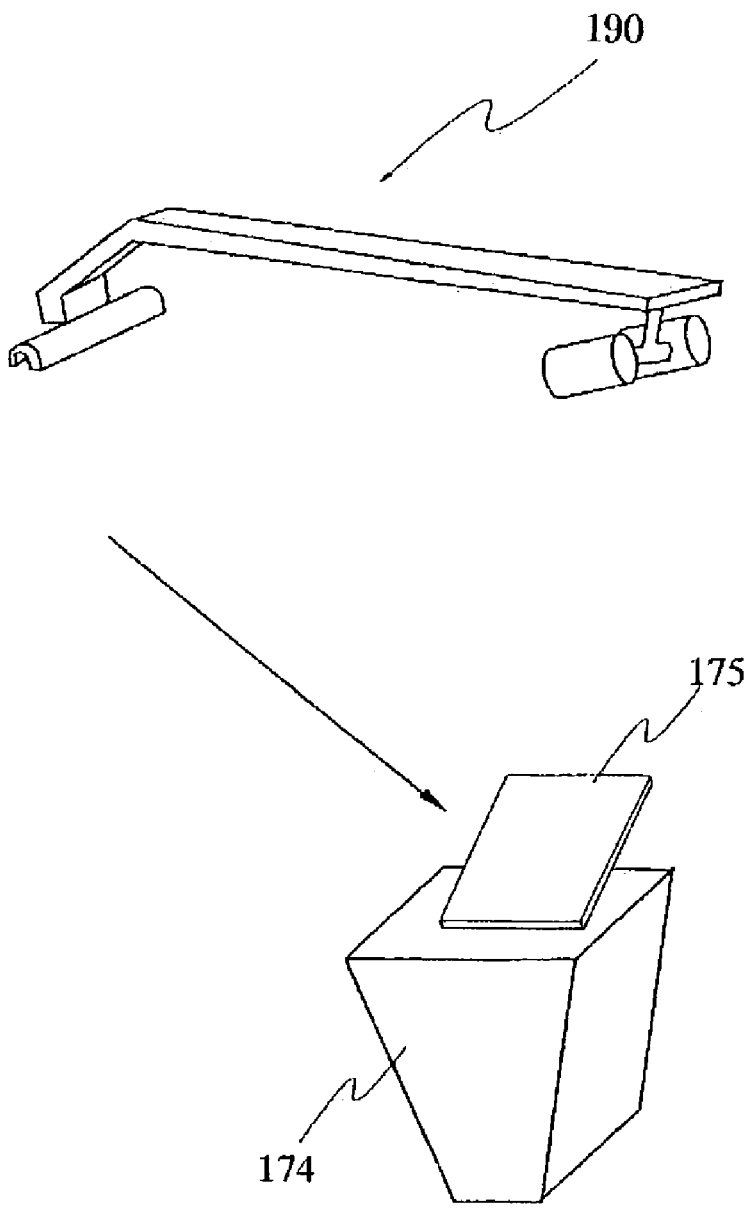
F I G. 2 3

THREE-DIMENSIONAL OBSERVATION APPARATUS AND METHOD OF THREE-DIMENSIONAL OBSERVATION

CROSS-REFERENCE TO RELATED APPLICATION

This application is based upon and claims the benefit of priority from prior Japanese Patent Application No. 2002-031426, filed Feb. 7, 2002, the entire contents of which are incorporated herein by reference.

BACKGROUND OF THE INVENTION

1. Field of the Invention

This invention relates to a three-dimensional observation apparatus and a method of three-dimensional observation. More particularly the invention relates to a three-dimensional observation apparatus and a method of three-dimensional observation useful for observing a medical image.

2. Description of the Related Art

There is a miniature three dimensional display apparatus called a head mount display as a means for observing an image three-dimensionally. This apparatus projects light beams from two images having parallax to each other on right and left pupils (eyes) of an observer which corresponds to the two images, respectively. The two images having parallax to each other are displayed on two image displays, respectively, and are directly projected on the pupils by the optical system arranged extremely near the face of the observer. Therefore, three-dimensional observation occurs as a virtual image which is equivalent to an image information of a big screen. This apparatus is hereinafter referred to as a HMD system.

Moreover, there is an apparatus to observe an image three-dimensionally by wearing glasses which has a shutter function. This apparatus displays images having parallax to each other on the monitor of the same position one after another. And an observer observes the monitor by wearing the glasses with the shutter function which synchronizes with switching one after another of the monitor's image and right and left are changed one after another. This apparatus is hereinafter referred to as a Monitor system.

As for HMD system and Monitor system, an observation optical system and glasses having a shutter function are arranged extremely near the front of a user's eyes because the same are worn by the user.

BRIEF SUMMARY OF THE INVENTION

This invention provides a three-dimensional observation apparatus comprising an optical reflection member which reflects a light beam and converges the light beam after the reflection; an image projector for a right eye which projects a medical image for the right eye on the optical reflection member and forms an exit pupil for the right eye at a position apart from the optical reflection member by a predetermined distance; and an image projector for a left eye which projects a medical image for the left eye on the optical reflection member and forms an exit pupil for the left eye at a position apart from the optical reflection member by a predetermined distance.

The apparatus also includes a holding member which keeps a positional relationship of the image projector for the right eye to the optical reflection member and a positional relationship of the image projector for the left eye to the optical reflection member.

BRIEF DESCRIPTION OF THE DRAWINGS

These and other features, and advantages of the instruments and methods of this invention will become better understood based on the following description, appended claims, and accompanying drawings wherein:

FIG. 10 illustrates a second modified example of the operating apparatus of FIG. 8.

FIG. 20 illustrates a tenth preferred embodiment of a construction of the operating apparatus of the present invention.

FIG. 21 is a first illustration to explain a disposable panel of an eleventh embodiment of the present invention.

FIG. 22 is a second illustration which explains the disposable panel of FIG. 21.

FIG. 23 is a third illustration which explains the disposable panel of FIG. 21.

DETAILED DESCRIPTION OF THE EXAMPLES OF THE INVENTION

Figure 1:
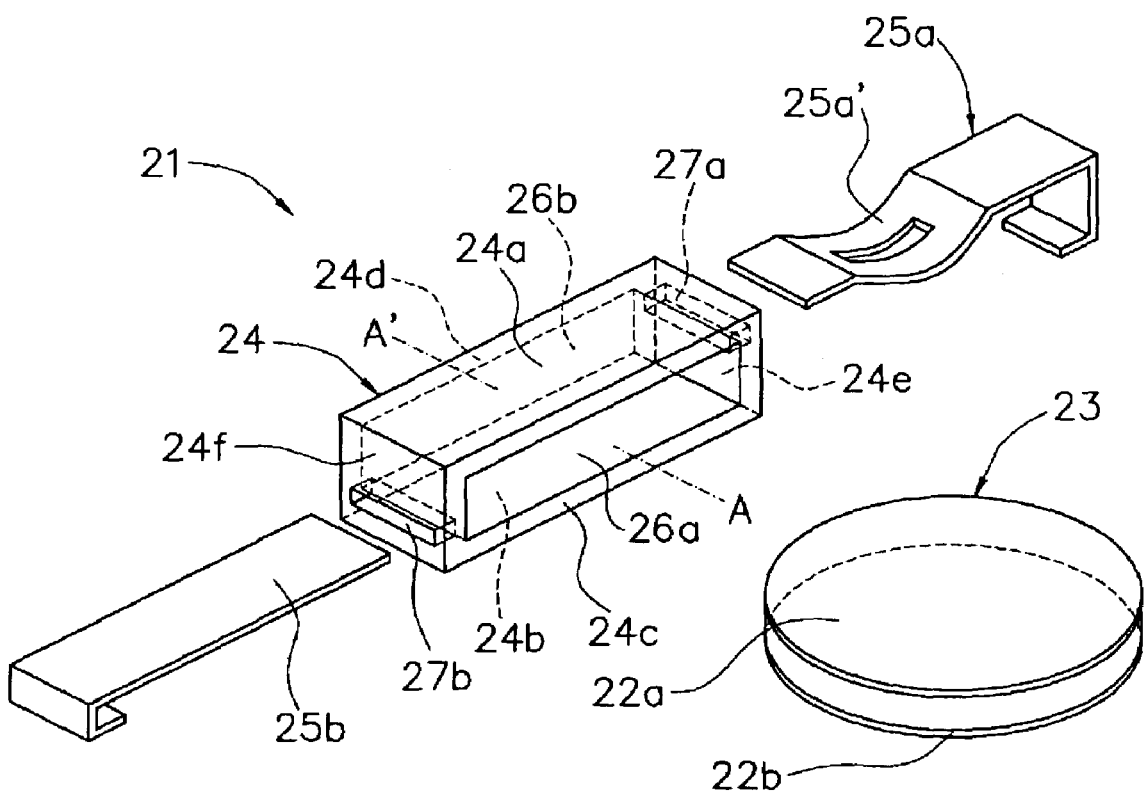
FIG. 1 illustrates an example of the principle of an optical system of the present invention.

First, the example of the optical system principle of this invention is explained by referring to FIG. 1. In FIG. 1, 1 is an observer, 2 is the right eye of the observer, 3 is a light reflection member (in this example, a Fresnel concave mirror panel), 4 is an image projector which corresponds to a right eye of the observer 1, 5 is an image display device, 6 is an image projection optical system, 7 is the image displayed on the image display, 8 is the image projected on the light reflection member by the image projection optical system, 9 is the exit pupil of the image projection optical system, 10 is a mirror coating, 11 is a Fresnel concave mirror having a positive power when viewed from the image projector, and 13 is the exit pupil of the image projection optical system projected by the Fresnel concave mirror. The illustration of the image projector which corresponds to the left eye of the observer is omitted in FIG. 1, however, such an image projector is substantially similar to that of the right eye shown in FIG. 1.

In FIG. 1 the image 7 displayed by the image display device 5 is projected by the image projection optical system 6, and is projected on the light reflection member. The Fresnel concave mirror 11, which comprises a light reflection member 3, projects the exit pupil 9 of the image projection optical system 6 on the right eye 2 of the observer 1 due to the lens action.

In other words, the light from the image projector is reflected, and the light is concentrated only around the right eye 2 of the observer 1. Therefore, the observer 1 can observe the image projected by the image projector 4 which corresponds to the right eye 2 of the observer 1 with the right eye 2. The image projected by the image projector which corresponds to the left eye can be observed with the left eye of the observer 1 in the same way through an image projector which corresponds to the left eye and the left eye of the observer 1. The right eye can't observe the image which the left eye can observe and vice versa. Therefore, a three-dimensional observation can be achieved by observing a different image which has parallax respectively with the right and left eyes.

Figure 2:
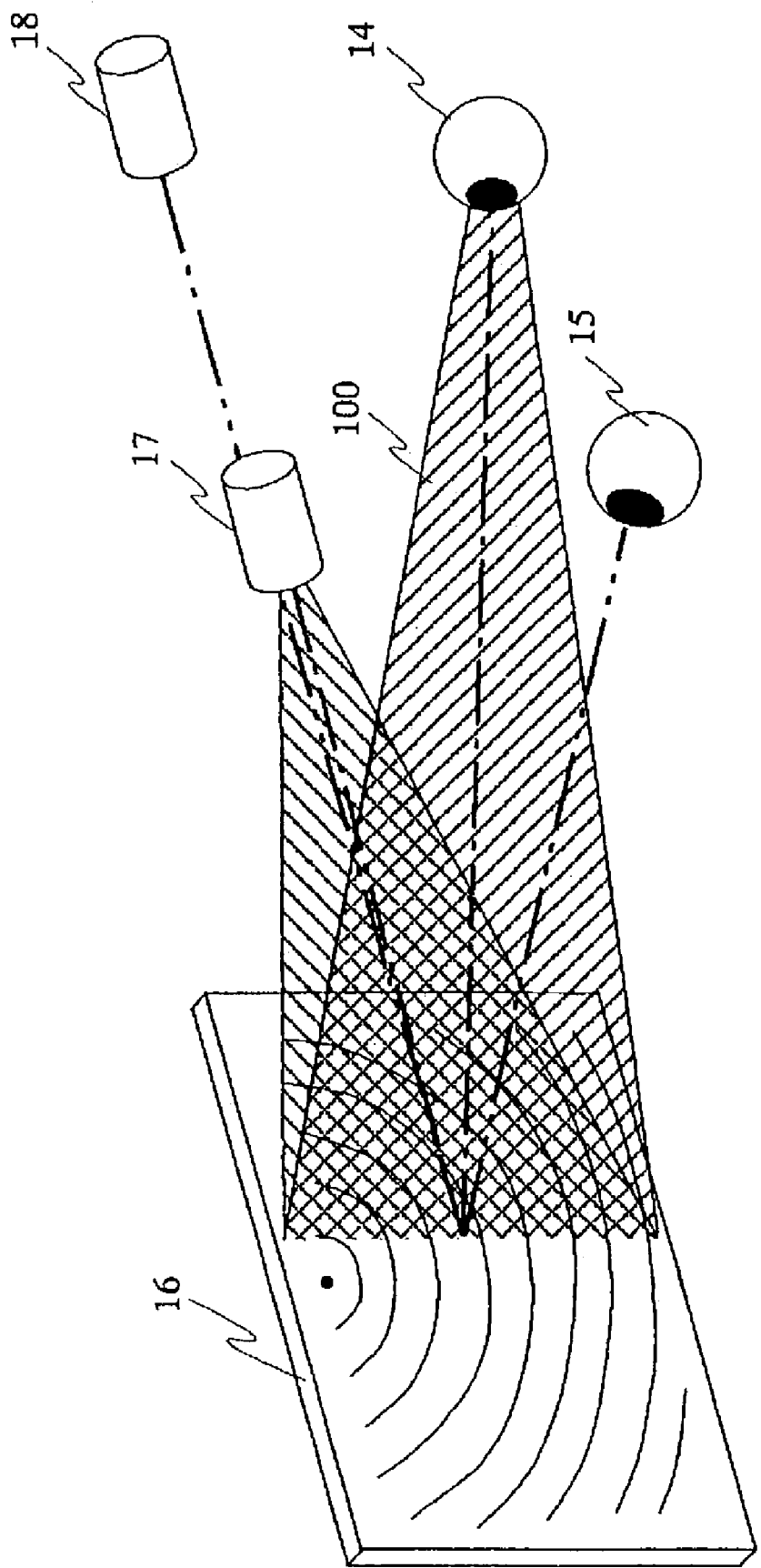
FIG. 2 is a perspective view to explain an example of an optical system of this invention.

FIG. 2 is a perspective view to explain an example of a preferred implementation of an optical system of the present invention. In FIG. 2, 14 is the right eye of the observer, 15 is the left eye of the observer, 16 is a light reflection member, 17 is the image projector which corresponds to the right eyes of the observer, 18 is the image projector which corresponds to the left eyes of the observer, 100 is the light beam which concentrates on the right eye of the observer after reflecting a light beam from the image projector which corresponds to the right eye of the observer.

FIG. 2 shows the three-dimensional arrangement of the optical system which isn't shown by FIG. 1.

Figure 3:
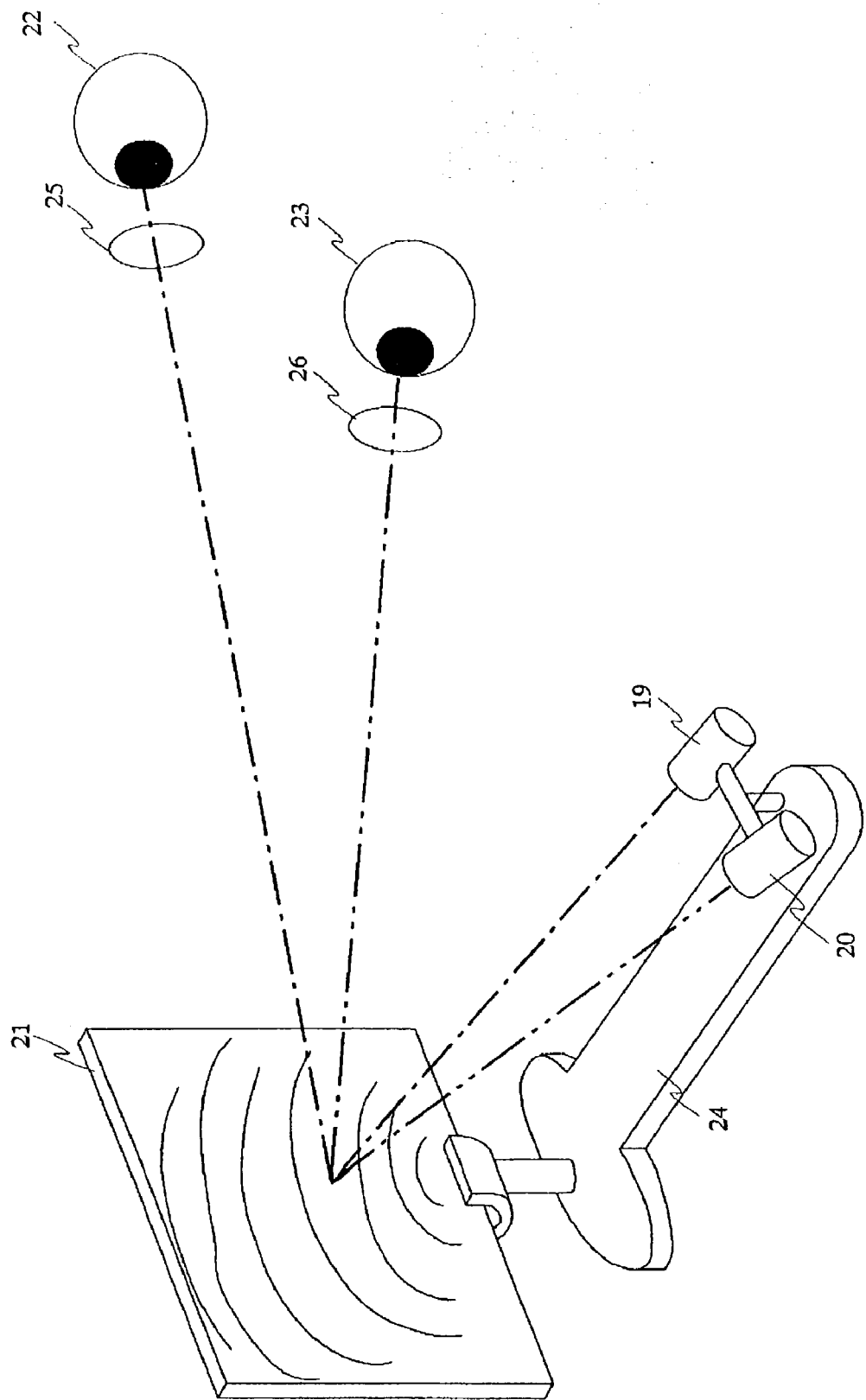
FIG. 3 is a perspective view to explain an example of a whole composition of the present invention.
Figure 4:
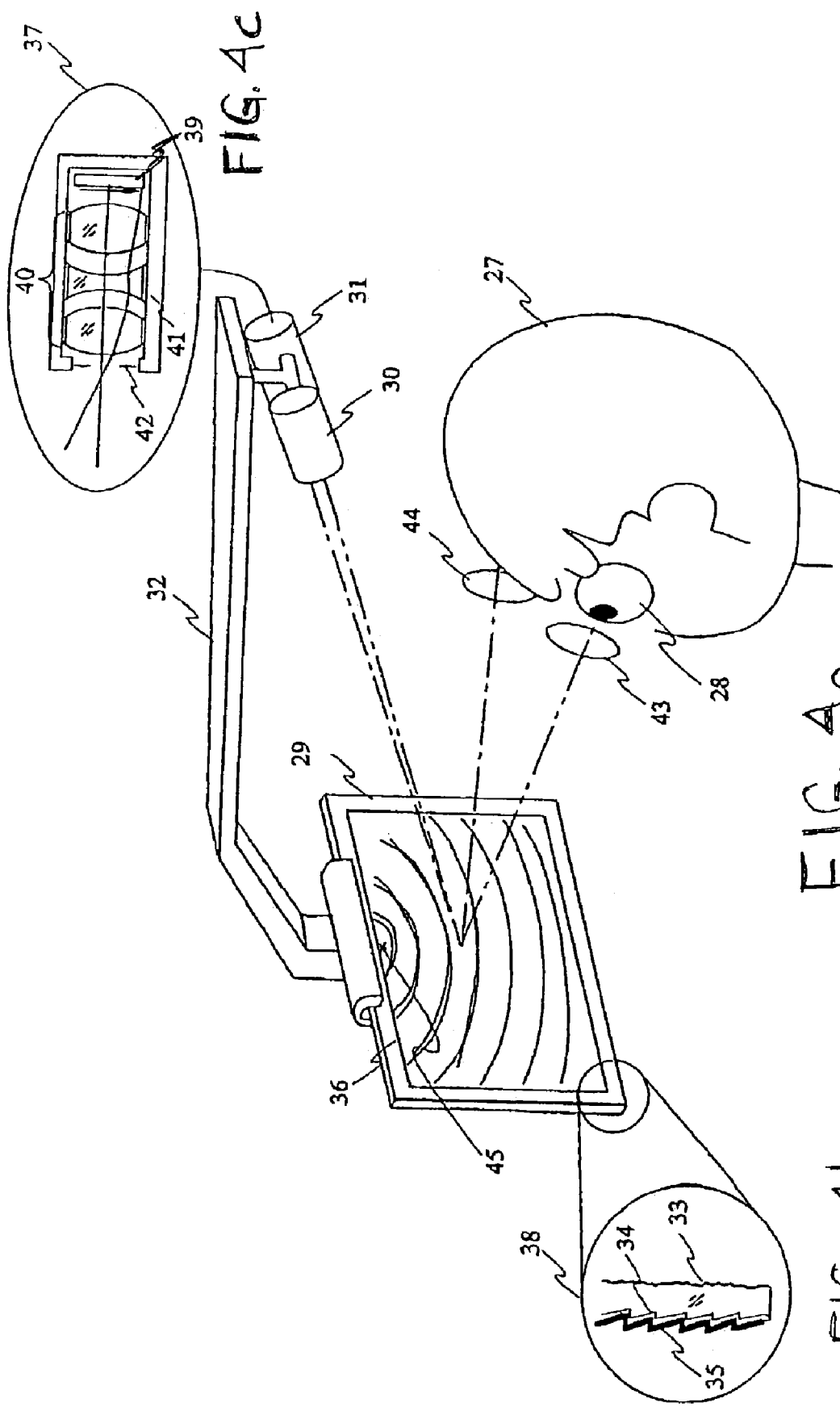
FIGS. 4a–4c show a first preferred embodiment of the three-dimensional observation apparatus of the present invention.

FIG. 3 is a perspective view to explain a preferred implementation of a whole composition of the present invention. In FIG. 3, 19 is the image projector for the left eye of the observer, 20 is the image projector for the right eye of the observer, 21 is a light reflection member, such as an image projection panel, 22 is the right eye of the observer, 23 is the left eye of the observer, 24 is the support member which supports two image projectors and a light reflection member, 25 is the exit pupil of the image projection optical system for the right eye 22, which is projected due to the lens action of the Fresnel concave mirror in the light reflecting member 21, and 26 is the exit pupil of the image projection optical system for the left eye 23, which is projected due to the lens action of the Fresnel concave mirror in the light reflecting member 21. The image projection optical systems built into the image projectors 29, 20 are not illustrated in FIG. 3 but are assumed to have a similar structure as that illustrated in FIG. 1.

In FIG. 3, a support member 24 supports the light reflection member 21 and image projectors 19,20 so that images projected by image projectors 19,20 are incident on substantially the same place on the light reflecting member 21 and the exit pupils of the image projection optical systems built in image projectors are projected in the position of the eye of the observer due to the lens action of the Fresnel concave mirror of the light reflecting member 21.

The operation of the apparatus of FIG. 3 will now be explained with reference to FIGS. 4a–6.

Figure 5:
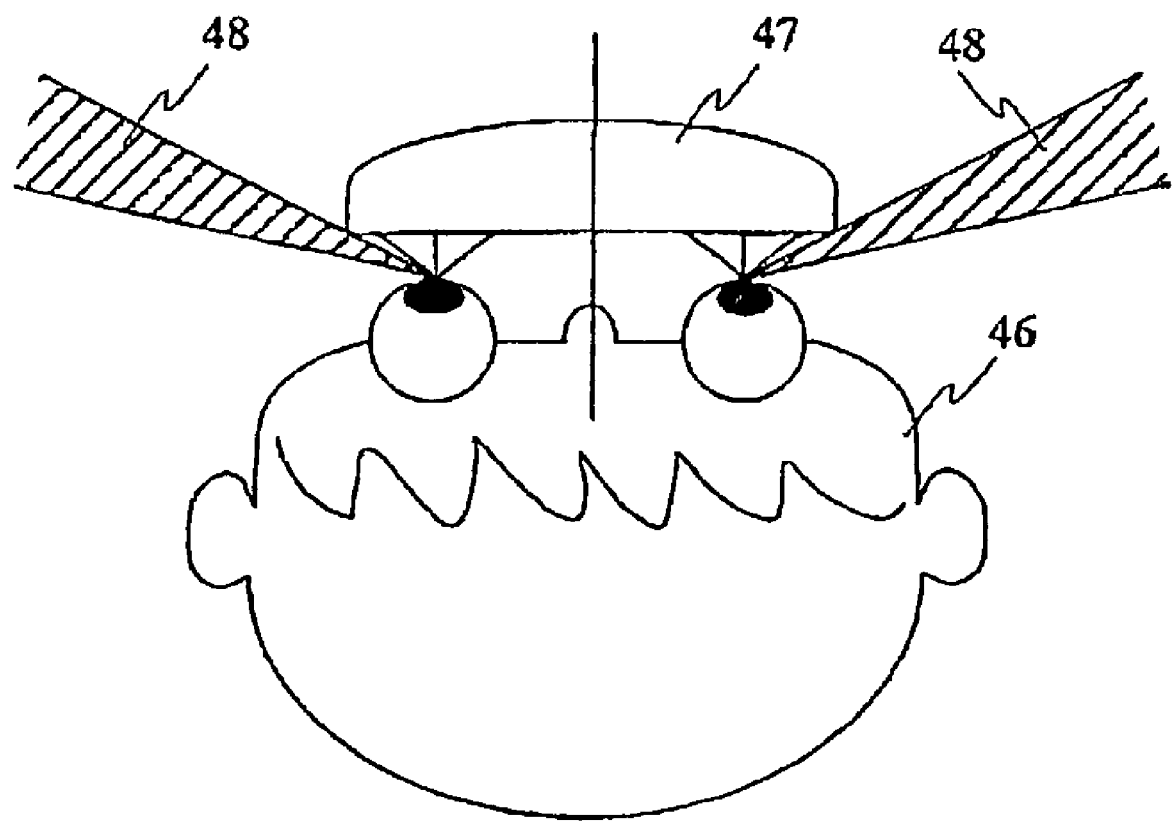
FIG. 5 is a first illustration to explain a function of the three-dimensional observation of FIG. 4.
Figure 6:
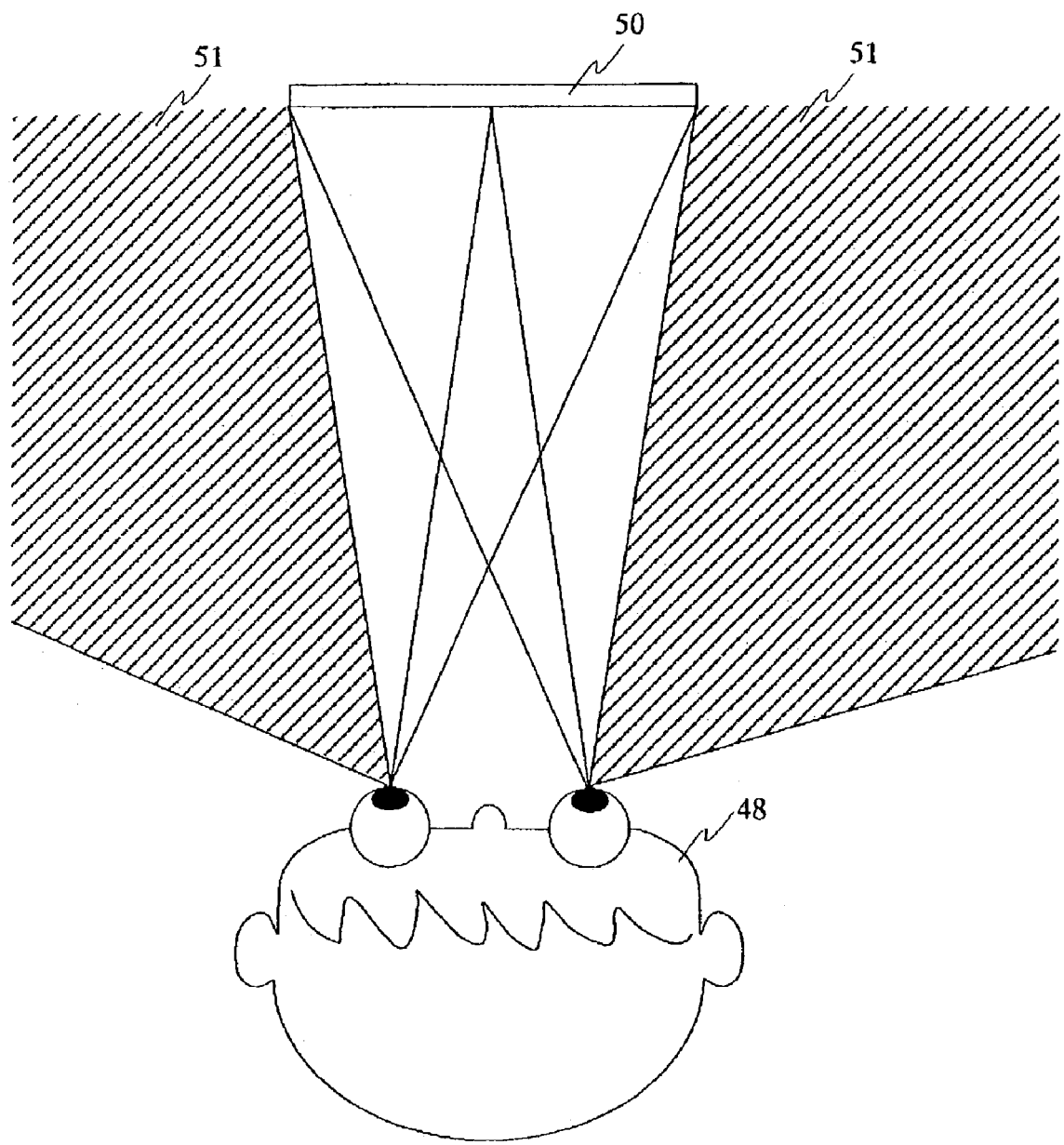
FIG. 6 is a second illustration to explain a function of the three-dimensional observation of FIG. 4.

FIGS. 4a–4c show the construction of the three-dimensional observation apparatus, FIG. 5 is a first figure in which the action of the three-dimensional observation apparatus of FIGS. 4a–4c is described. FIG. 6 is a second figure in which the action of the three-dimensional observation apparatus of FIGS. 4a–4c is described.

In FIGS. 4a–4c, 27 is an observer, 28 is the left eye of the observer, 29 is an image projection panel, 30 is the image projector which corresponds to the right eyes of the observer 27, 31 is the image projector which corresponds to the left eye 28 of the observer 27, 32 is the support arm which supports an image projection panel 29 and image projectors 30 and 31, 33 is a diffusion surface of the image projection panel 29, 34 is the Fresnel lens side of the image projection panel 29, 35 is an aluminum evaporation coating, 36 is the image projected by the image projector 30 for the right eye and the image projector 31 for the left eye, which is formed by projecting the two images from the image projectors 30 and 31 to be incident substantially on the same place on the image projection panel 29, 37 is the optical system components of the image projectors 30 and 31, 38 is the expanded sectional view of the image projection panel 29, 39 is a miniature LCD, 40 is a projection optical system, 41 is the frame in which the miniature LCD 39 and the projection optical system 40 are supported, 42 is the exit pupil of the projection optical system 40, 43 is the exit pupil of the projection optical system built in the image projector 31 which corresponds to the left eye 28 of the observer 27 and is projected due to the lens action of the image projection panel 29, 44 is the exit pupil of the projection optical system built in the image projector 30 which corresponds to the right eye of the observer 27 and is projected due to the lens action of the image projection panel 29, and 45 is a center of the Fresnel lens of the image projection panel 29.

The two image projectors 30 and 31 display the image 36 which has parallax to each other on the miniature LCD 39 disposed therein. Then, as it is shown by the expansion cross section 37, an optical system 40 projects the image 36 on the projection image projection panel 29. The image projection panel 29 is composed by a diffusion surface 33 and a Fresnel lens surface 34 in this order when it is viewed from the side of the image projectors 30 and 31.

Furthermore, the Fresnel lens surface 34 is given an aluminum evaporation coating 35, therefore, it is configured as a Fresnel concave mirror having a positive power when it is viewed from the side of the image projectors 30 and 31. A support arm 32 supports the image projection panel 29 from a ceiling, wall or other support structure. The support arm 32 also supports the image projectors 30,31 so that images projected by the image projectors 30,31 are incident on substantially the same place on the light reflecting member 21 and the exit pupils of the image projection optical systems built in the image projectors 30, 31 are projected in the position of the eye of the observer 27 due to the lens action of the Fresnel concave mirror of the image projection panel 29.

The exit pupils 43, 44 of the projection optical systems of the image projector 30, 31 projected due to the lens action of the image projection panel 29 are magnified due to the optical diffusion action of the diffusion surface 33 of the image projection panel 29.

According to this structure, the light beams projected from both of the image projectors 30 and 31 are reflected by the Fresnel concave mirror of the image projection panel 29, and converge around the respective eyes of the observer 27. Therefore, the observer 27 can observe only the image projected by the image projector 30 by the left eye and can observe only the image projected by the image projector 31 by the right eye. Therefore, a three-dimensional image can be observed without attaching an observation optical system such as a HMD system, or the glasses which have a shutter function such as a Monitor system to the face. Also, stoppages in the flow of the work can be prevented because an attaching and detaching of the glasses becomes unnecessary when a three-dimensional image isn't being observed.

As shown in FIG. 5, a HMD system of the prior art partially interrupts the sight of the observer 27 for the three dimensional image observation because the HMD three-dimensional observation apparatus 47 which builds in LCD and an observation optical system is arranged in front of the observer's eyes. The LCD and the observation optical system aren't illustrated in FIG. 5. As can be seen in FIG. 5, observation by both eyes is restricted to sight areas 48.

Because of this, surrounding conditions except for the image cannot be seen, and a communication with the assistant who is in the surroundings of the observer cannot be done while doing work such as-an operation and observing a three-dimensional image.

As described in FIG. 6, according to a preferred implementation of a three-dimensional observation apparatus of the first embodiment, a distance from the observer 48 to the image display panel 50 (in this embodiment, for example, about 450 mm) can be maintained. Therefore, the sight interruption of the observer 48 is kept to a minimum and observation by both eyes is possible even with the remaining sight 51 during the three-dimensional observation.

Figure 7:
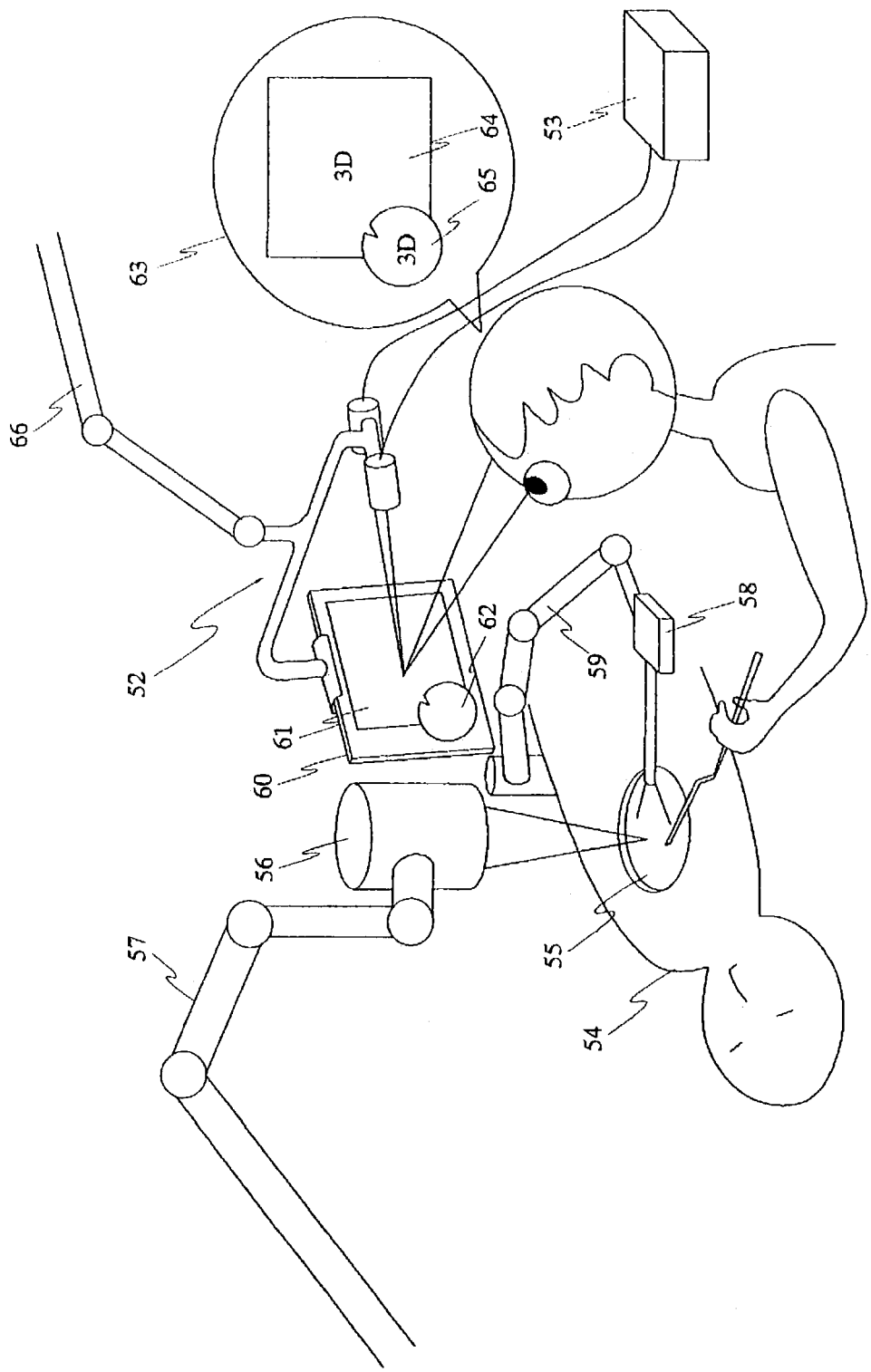
FIG. 7 illustrates a second preferred embodiment of a construction of the operating apparatus of the present invention.

FIG. 7 shows a preferred structure of an operating device concerned with a second embodiment of this invention.

Because the second embodiment is similar in structure to the first embodiment described above, only differences are explained, the same numbers are given to the same structure, and an explanation thereof is omitted.

In FIG. 7, 52 is the three-dimensional observation apparatus explained above with regard to the first embodiment, 53 is a controller which displays an image in the miniature LCD 39 that the three-dimensional observation apparatus 52 projects to the right and left eyes of the observer, 54 is a person being operated on, 55 is a surgical site on the person 54, 56 is a stereo microscope for the operation which three-dimensionally picks up the image of surgical site 55, 57 is a support arm which supports the stereo microscope 56 for the operation, 58 is a stereo-endoscope which three-dimensionally picks up an image of the surgical site 55, 59 is a support arm which supports a stereo-endoscope 58, 60 is the image projection panel of the three-dimensional observation apparatus 52, 61 is the image of the stereo microscope 56 for the operation projected on the image projection panel 60, 62 is the image of the stereo-endoscope 58 projected on the image projection panel 60, 63 is the image which the observer observes, 64 is the three dimensional image of the stereo microscope 56 for the operation, 65 is the three-dimensional image of the stereo-endoscope 58, 66 is a support arm which supports the three-dimensional observation apparatus 52.

The stereo microscope 56 for the operation and/or the stereo-endoscope 58 pick up a pair of images of the surgical site by the CCD which is built in, respectively, and which isn't illustrated. The images picked up from the stereo microscope 56 and stereo-endoscope 58 are sent to the controller 53.

Moreover, the controller sends the image to the miniature LCD 39 in the three-dimensional observation apparatus 52 which displays the same.

Thus, the image picked up by the stereo microscope 56 for the operation and/or the stereo-endoscope 58 can be observed three-dimensionally without attaching 3-D glasses to his/her face having an observation optical system or shutter function.

Figure 8:
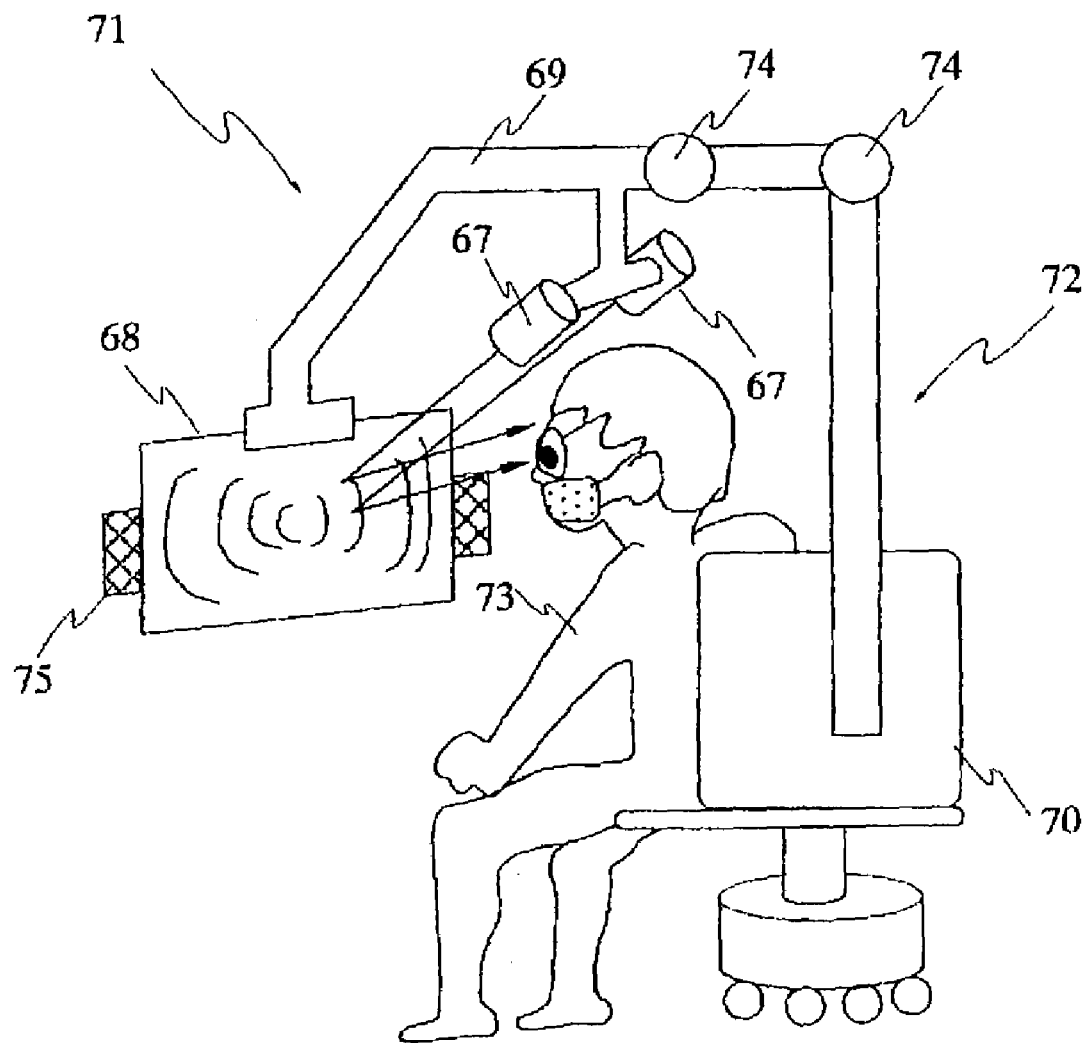
FIG. 8 illustrates a third preferred embodiment of a construction of the operating apparatus of the present invention.
Figure 9:
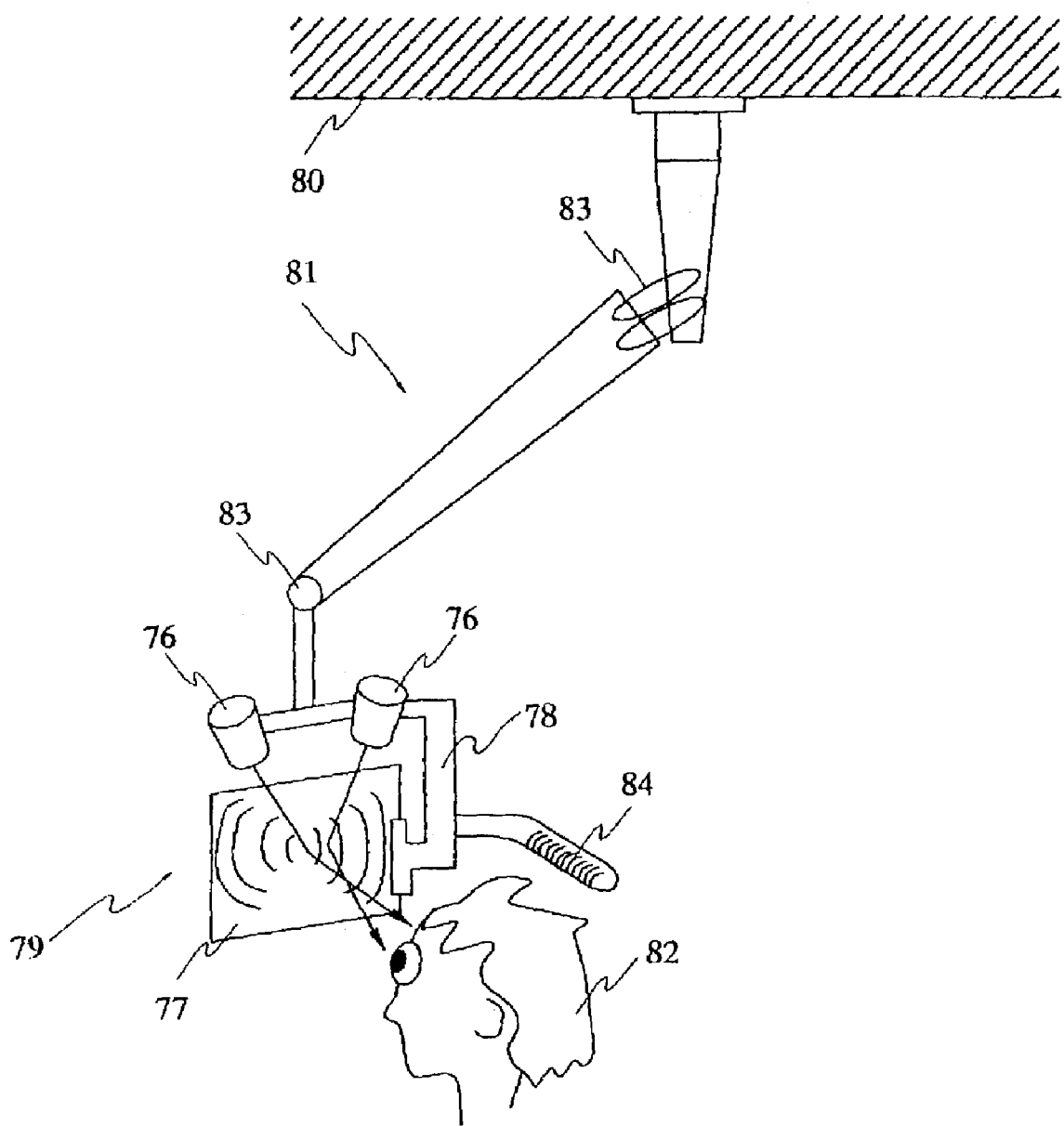
FIG. 9 illustrates a first modified example of the operating apparatus of FIG. 8.

FIG. 8 to FIG. 10 are concerned with a third embodiment of the present invention, where FIG. 8 shows the structure of the operating device, FIG. 9 shows a first modified example of the operating device of FIG. 8, and FIG. 10 shows a second modified example of the operating device of FIG. 8.

Because the third embodiment is similar in structure to the first embodiment described above, only differences are explained, the same numbers are given to the same structure, and an explanation thereof is omitted.

In FIG. 8, 67 are image projectors, 68 is an image projection panel, 69 is the support arm which supports the image projector 67 and an image projection panel 68, 70 is a chair for the operation, 71 is a three-dimensional observation apparatus, 72 is a second support arm which fixes the position of the three-dimensional observation apparatus 71 to the chair 70 for the operation where the fixed position is adjustable, 73 is an observer, 74 are joints of the second support arm 72, 75 is a holding portion which is gripped by the observer (or other user) to move or otherwise adjust the position of the three-dimensional observation apparatus 71.

Moreover, in FIG. 9 which shows a first modified example of the third embodiment, 76 are image projectors, 77 is an image projection panel, 78 is a support arm which supports the image projector 76 and the image projection panel 77, 79 is a three-dimensional observation apparatus, 80 is the ceiling of the operating room, 81 is a second support arm which fixes the position of the three-dimensional observation apparatus 79 to the ceiling 80 of the operating room where the fixed position is adjustable, 82 is an observer, 83 is a joint of the second support arm 81, 84 is the grip which is gripped to move the three-dimensional observation apparatus 79.

Moreover, in FIG. 10, which shows a second modified example of the third embodiment, 85 are image projectors, 86 is an image projection panel, 87 is a support arm which supports the image projector 85 and the image projection panel 86, 88 is a three-dimensional observation apparatus, 89 is the wall of the operating room, 90 is the second support arm which fixes the position of the three-dimensional observation apparatus 88 to the wall 89 of the operating room where the fixed position is adjustable, 91 is an observer, 92 are joints of the second support arm 90, 93 is a grip which is gripped to move the three-dimensional observation apparatus 88.

According to these structures, the observer can always use the three-dimensional observation apparatus in a position that is easy to observe and can move it quickly to a position where it doesn't become an obstacle from the front of the observer's eyes when the three-dimensional observation is unnecessary.

Figure 11:
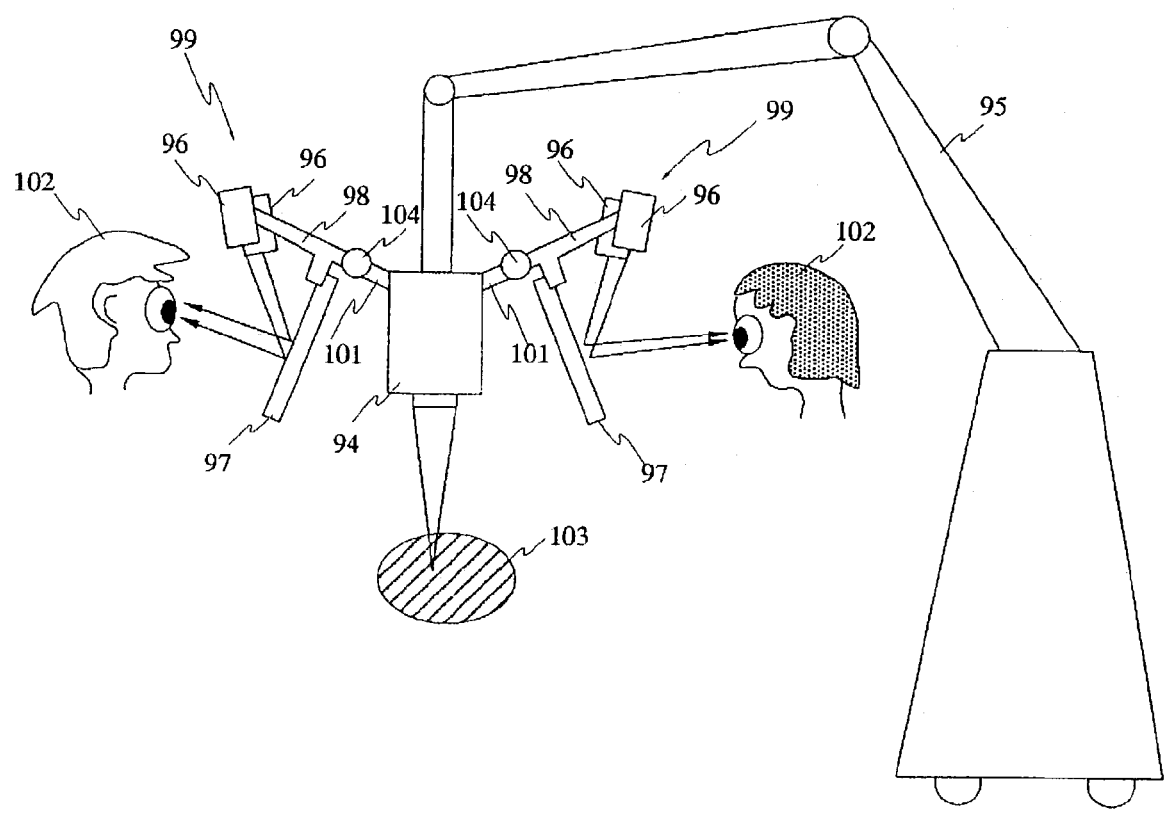
FIG. 11 illustrates a forth preferred embodiment which shows a construction of an operating apparatus of the present invention.

FIGS. 11–FIG. 14 are concerned with a fourth embodiment of the present invention, and FIG. 11 shows the structure of the operating device.

Figure 12:
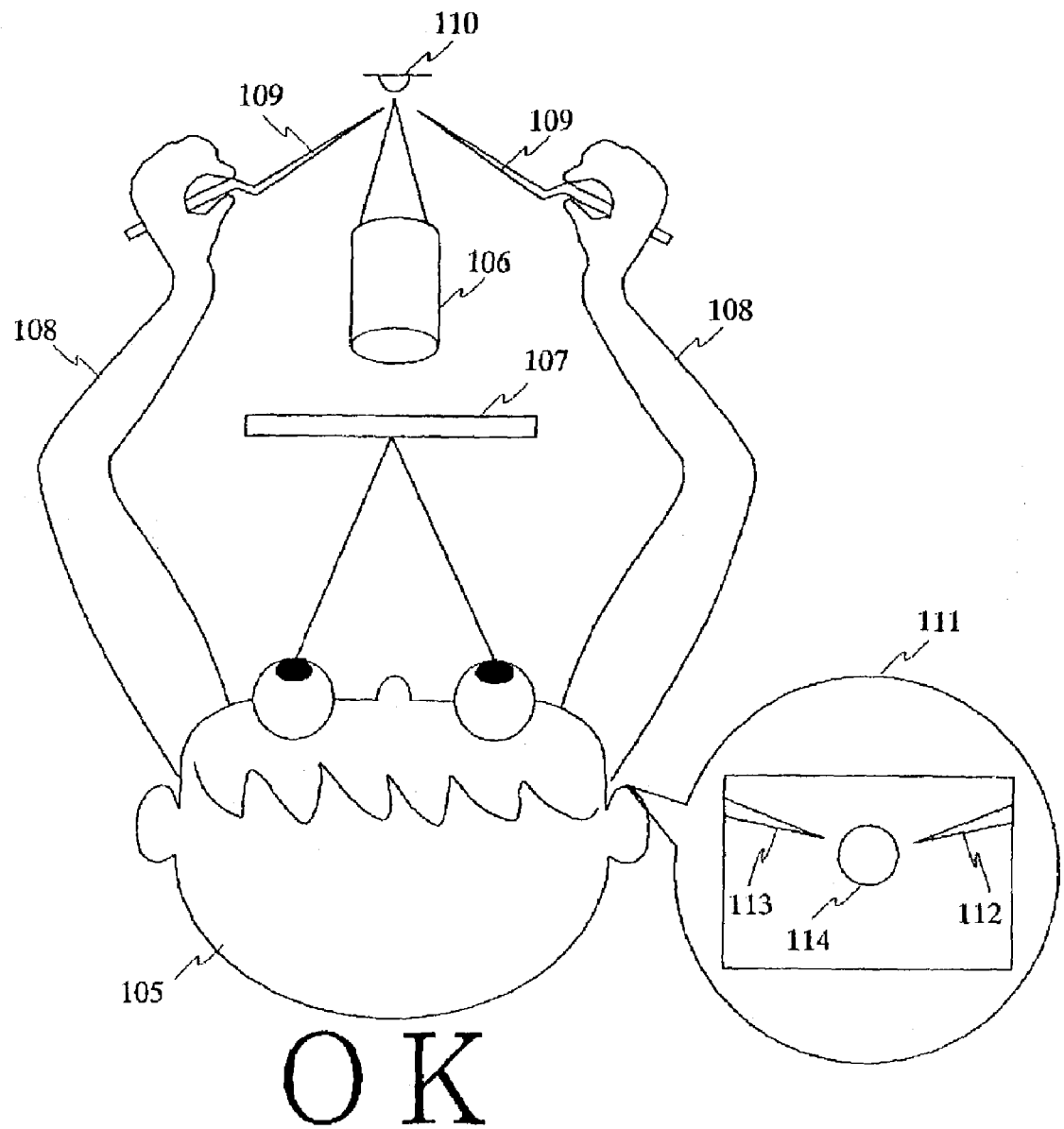
FIG. 12 is a first illustration to explain a function of the operating apparatus of FIG. 11.
Figure 13:
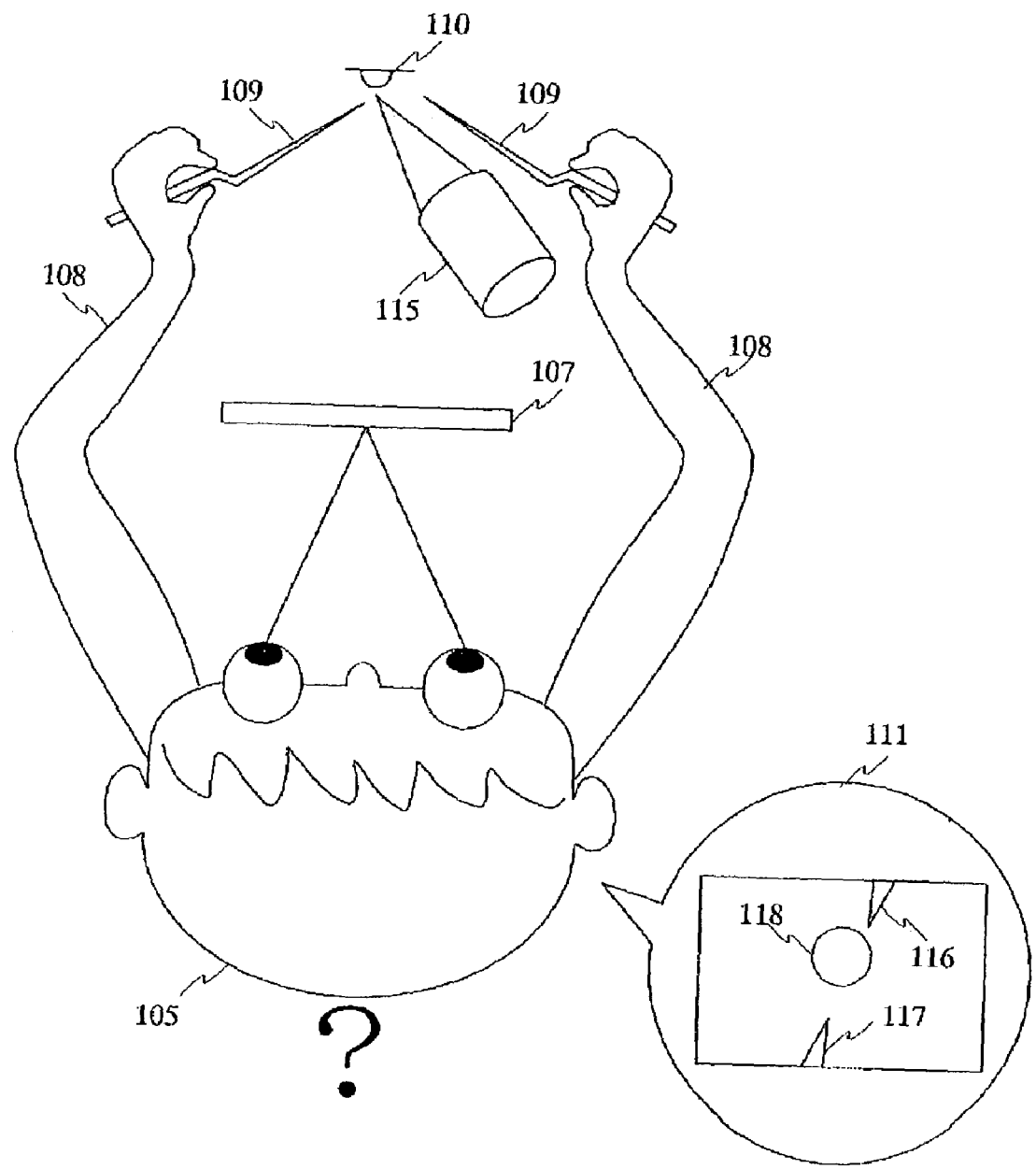
FIG. 13 is a second illustration to explain a function of the operating apparatus of FIG. 11.
Figure 14:
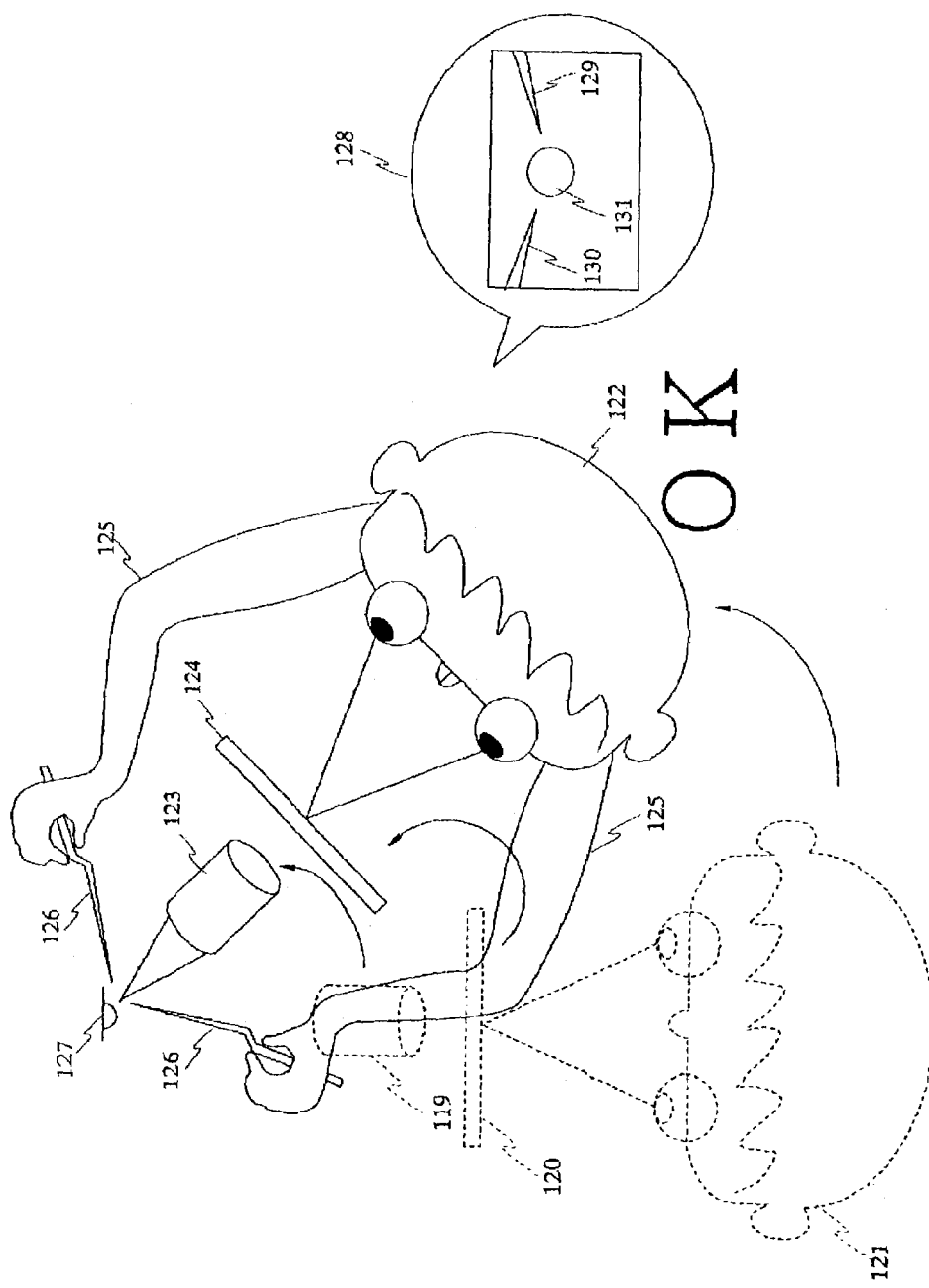
FIG. 14 is a third illustration to explain a function of the operating apparatus of FIG. 11.

FIG. 12 is a first figure in which the action of the operating device of FIG. 11 is shown, and FIG. 13 is a second figure in which the action of the operating device of FIG. 11 is shown, and FIG. 14 is a third figure in which the action of the operating device of FIG. 11 is shown.

Because the fourth embodiment is similar in structure to the first embodiment discussed above, only differences are explained, the same numbers are given to the same structure, and an explanation thereof is omitted.

In FIG. 11, 94 is a stereo microscope for viewing an operation, 95 is a support arm of the stereo microscope 94 for the operation, 96 are image projectors, 97 are image projection panels, 98 are support arms which support the image projectors 96 and the image projection panel 97, 99 are three-dimensional observation apparatus, 101 are second support arms which fix the position of the three-dimensional observation apparatus 99 to the stereo microscope for the operation 94 where the fixed position is adjustable, 102 are observers, 103 is an observed object, and 104 are joints of the second support arms 101.

According to this structure, the observer can always use the three-dimensional observation apparatus in the position easy to observe and can move it quickly to a position where it doesn't become an obstacle in the front of the observer's eyes when the three-dimensional observation is unnecessary.

Furthermore, the three-dimensional observation apparatus 99 are moved by the movement of the stereo microscope 94 for the operation because the position of the stereo microscope 94 for the operation is fixed to the three-dimensional observation apparatus 99. Therefore, the observers 102 move their body to use the three-dimensional observation apparatus 99 moved with the stereo microscope for the operation 94. Therefore, as the direction of an observer 102 aligns with the direction where a stereo microscope for the operation picks up the image, a big deviation doesn't occur between the orientation of the image being watched and the orientation of a working hand and the work can be continued efficiently.

FIG. 12 and FIG. 13 show a three-dimensional observation apparatus which isn't moved by the movement of the stereo microscope for the operation.

FIG. 12 shows the stereo microscope for the operation before moving and FIG. 13 shows the stereo microscope movement for the operation after moving.

In FIG. 12, 106 is a stereo microscope for the operation, 107 is the image projection panel of the three-dimensional observation apparatus, 108 is the hand of the observer 105, 109 is an instrument for treatment, 110 is a surgical site, 111 is the image which an observer 105 is doing a three-dimensional observation, 112 is the projected three-dimensional image of the instrument for treatment which the observer has in his or her right hand, 113 is the projected three-dimensional image of the instrument for treatment which the observer has in his or her left hand, and 114 is the projected three-dimensional image of the surgical site. In FIG. 13, 115 is a stereo microscope for the operation that has been moved from the position shown in FIG. 12, 116 is the three-dimensional image of the instrument for treatment which the observer has in his or her right hand taken by the moved stereo microscope for the operation 115, 117 is the image of the instrument for treatment which the observer has in his or her left hand taken by the moved stereo microscope for the operation 115, 118 is the image of the surgical site taken by the moved stereo microscope for the operation 115.

In FIG. 12, the direction of the right hand of the three-dimensional observation is oriented with the direction of the right hand of the observer 105, and work is done easily.

In FIG. 13 the direction of the right hand of the three-dimensional observation is not oriented with the direction of the right hand of the observer 105 at all, and work can't be done easily.

FIG. 14 shows that a three-dimensional observation apparatus moves along with the movement of the stereo microscope for the operation.

In FIG. 14, 119 is a stereo microscope for the operation before it is moved, 120 is the position of the image projection panel before a stereo microscope for the operation 119 is moved, 121 is the position of the observer before a stereo microscope for the operation 119 is moved, 122 is the observer after a stereo microscope for the operation 119 is moved, 123 is the stereo microscope for the operation was after being moved, 124 is the image projection panel after the stereo microscope for the operation has been moved, 125 is the hand of the observer, 126 is an instrument for treatment, 127 is a surgical site, 128 is the three-dimensional image which the observer observes, 129 is the projected three-dimensional image of the instrument for treatment which the observer has in his or her right hand, 130 is the projected three-dimensional image of the instrument for treatment which the observer has in his or her left hand, and 131 is the projected three-dimensional image of the surgical site.

In FIG. 14, the image projection panel also moves following the movement of the stereo microscope for the operation. Therefore, the observer moves a body so as to see the image projected on the image projection panel. Thus, orientation of the right hand of the three-dimensional observation always aligns with the orientation of the right hand of the observer, and work can be done easily.

Figure 15:
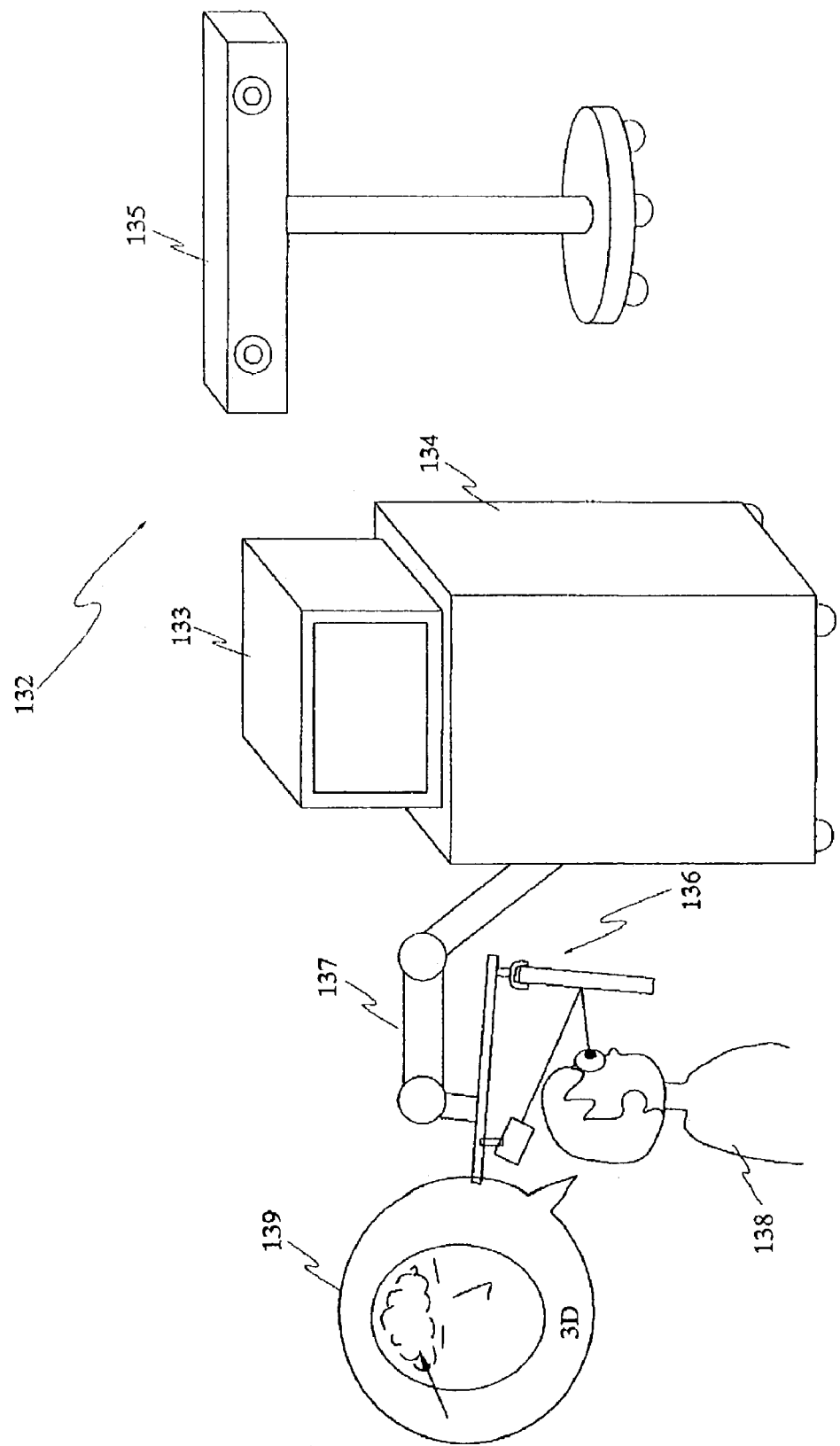
FIG. 15 illustrates a fifth preferred embodiment of a construction of the operating apparatus of the present invention.

FIG. 15 shows the structure of an operating device concerned with a fifth embodiment of the present invention.

Because the fifth embodiment is similar in structure to that of the first embodiment, only differences are explained, the same numbers are given to the same structure, and an explanation thereof is omitted.

In FIG. 15, 132 is an operating navigation system which includes a computer for creating a three dimensional image based on a CT•MR image of the patient obtained before the operation, 133 is a TV monitor, 134 is a trolley which holds the computer, 135 is a position detection camera array, 136 is a three-dimensional observation apparatus, 137 is a support arm which fixes the position of the three-dimensional observation apparatus 136 to the trolley 134, 138 is an observer, and 139 is the three-dimensional observation image which the observer 138 observes.

The operating navigation system 132 creates two images based on the CT•MR image of the patient obtained before the operation and viewed from two different points. These two images have parallax to each other and they are observed by the observer 138 with the three-dimensional observation apparatus 136. Therefore, the observer 138 can three-dimensionally observe an image which the operating navigation system 132 has created three-dimensionally, and can observe the image in a more realistic focus.

Figure 16:
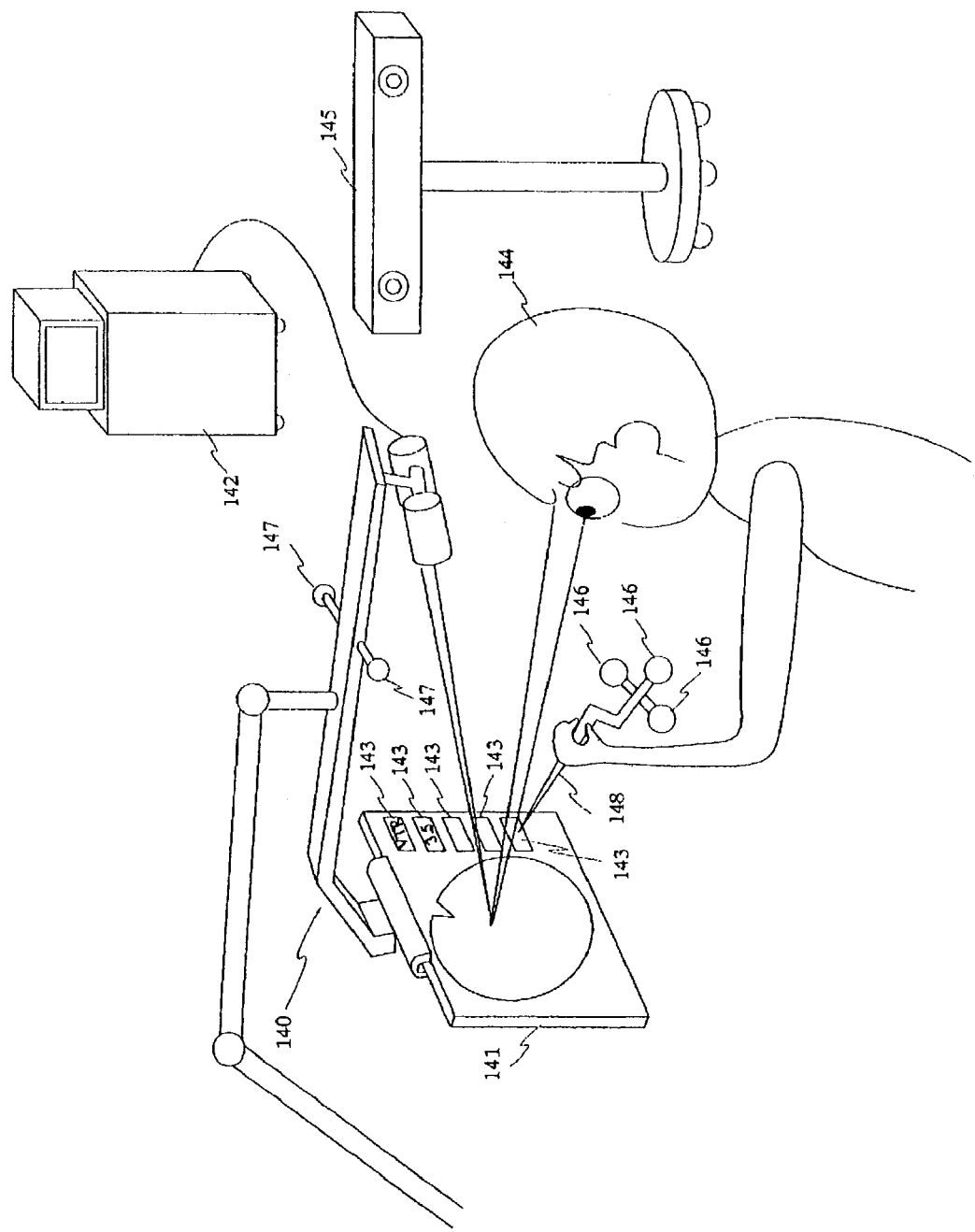
FIG. 16 illustrates a sixth preferred embodiment of a construction of the operating apparatus of the present invention.

FIG. 16 shows the structure of an operating device concerned with a sixth embodiment of the present invention.

Because the sixth embodiment is similar in structure to that of the first embodiment, only differences are explained, the same numbers are given to the same structure, and an explanation thereof is omitted.

In FIG. 16, 140 is a three-dimensional observation apparatus, 141 is an image projection panel of the three-dimensional observation apparatus 140, 142 is an operating navigation system, 143 are icons which the operating navigation system 142 projects on the image projection panel 141 through the three-dimensional observation apparatus 140, 144 is an observer, 145 is the position detection camera array of the operating navigation system 142, 148 is an instrument for treatment, 146 is a marker marked on the instrument for treatment 148, 147 is a marker marked on the three-dimensional observation apparatus 140.

The operating navigation system 142 generates the icon 143 to display on the three-dimensional observation apparatus 140 where the icons assign the operating control of the machine to the three-dimensional observation apparatus 140. The image of the icons 143 are preferably displayed as an unchanged image with no parallax even if it is viewed with the right eyes or viewed with the left eyes.

Moreover, the position detection camera array 145 picks up the marker 147 marked on the three-dimensional observation apparatus and detects the position of the icons 143 being projected on the image display panel 141.

Moreover, the position detection camera array 145 picks up the marker 146 marked on the three-dimensional observation apparatus and also detects a tip position of the instrument 148.

Furthermore, the function control which is assigned to each of the icons is carried out when the position of the icon and the position of the instrument 148 are same. Therefore the observer 144 can control the machine by touching an icon 143 with the tip of the instrument 148 when the observer wants to start or stop any function of the machine.

As it is not necessary to put a console around the surgical site separately, a three-dimensional observation apparatus can be made into a virtual console.

Figure 17:
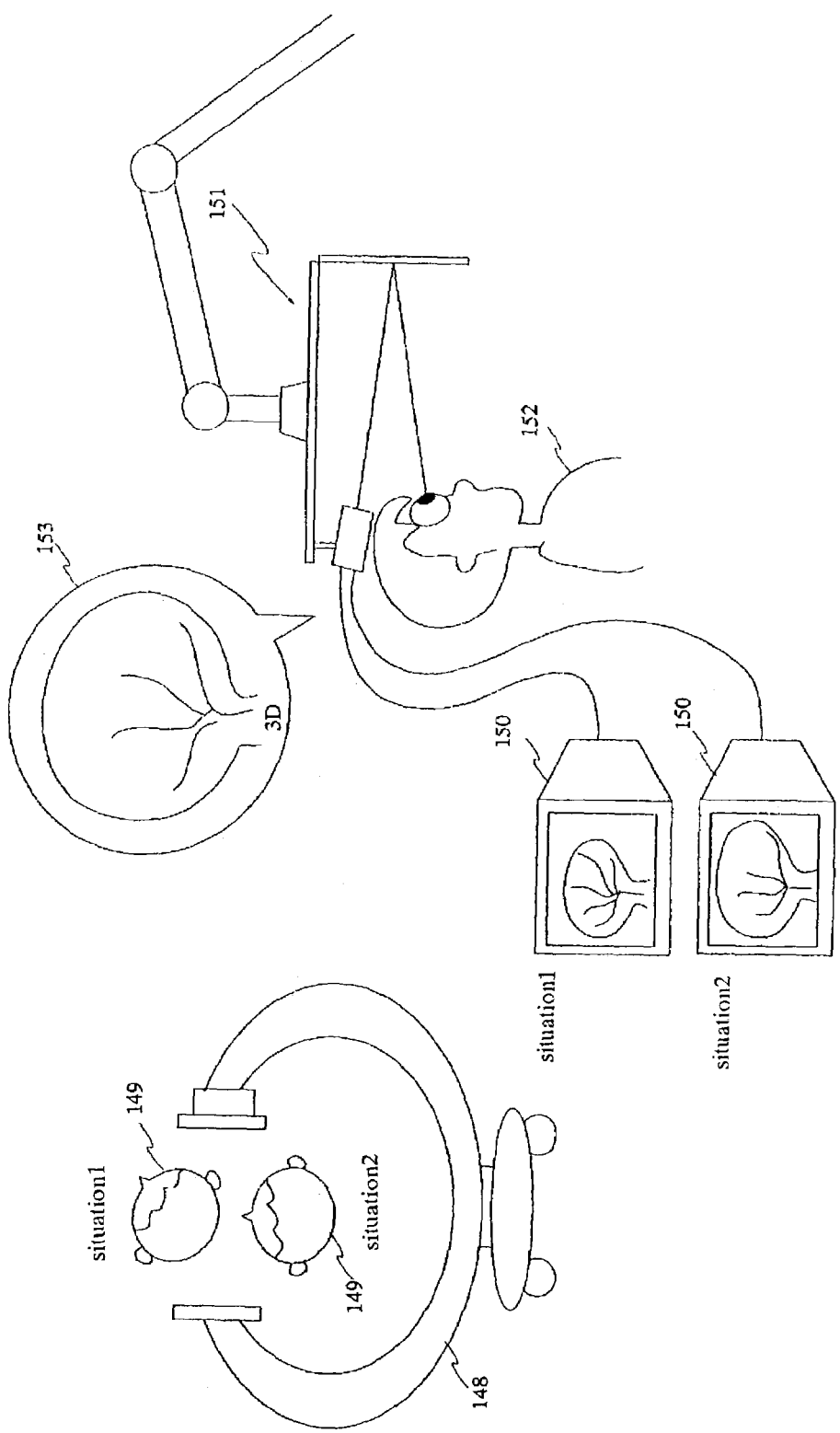
FIG. 17 illustrates a seventh preferred embodiment of a construction of the operating apparatus of the present invention.

FIG. 17 shows the structure of an operating device concerned with a seventh embodiment of the present invention.

Because the seventh embodiment is similar in structure to that of the first embodiment, only differences are explained, the same numbers are given to the same structure, and an explanation thereof is omitted.

In FIG. 17, 148 is an X-ray photographic device, 149 is a patient who has taken X-ray pictures using the X-ray photographic device 148, 150 is the taken X-ray picture, 151 is a three-dimensional observation apparatus, 152 is an observer, and 153 is a three-dimensional X-ray picture which an observer observes. The X-ray picture 150 is taken from two directions of the patient 149 with the X-ray photographic device 148. These two X-ray pictures have parallax, and they are displayed with the three-dimensional observation apparatus 151.

According to this structure, the image picked up by the X-ray photographic device 148 can be observed three-dimensionally without attaching glasses that have an observation optical system or shutter function to the face.

Figure 18:
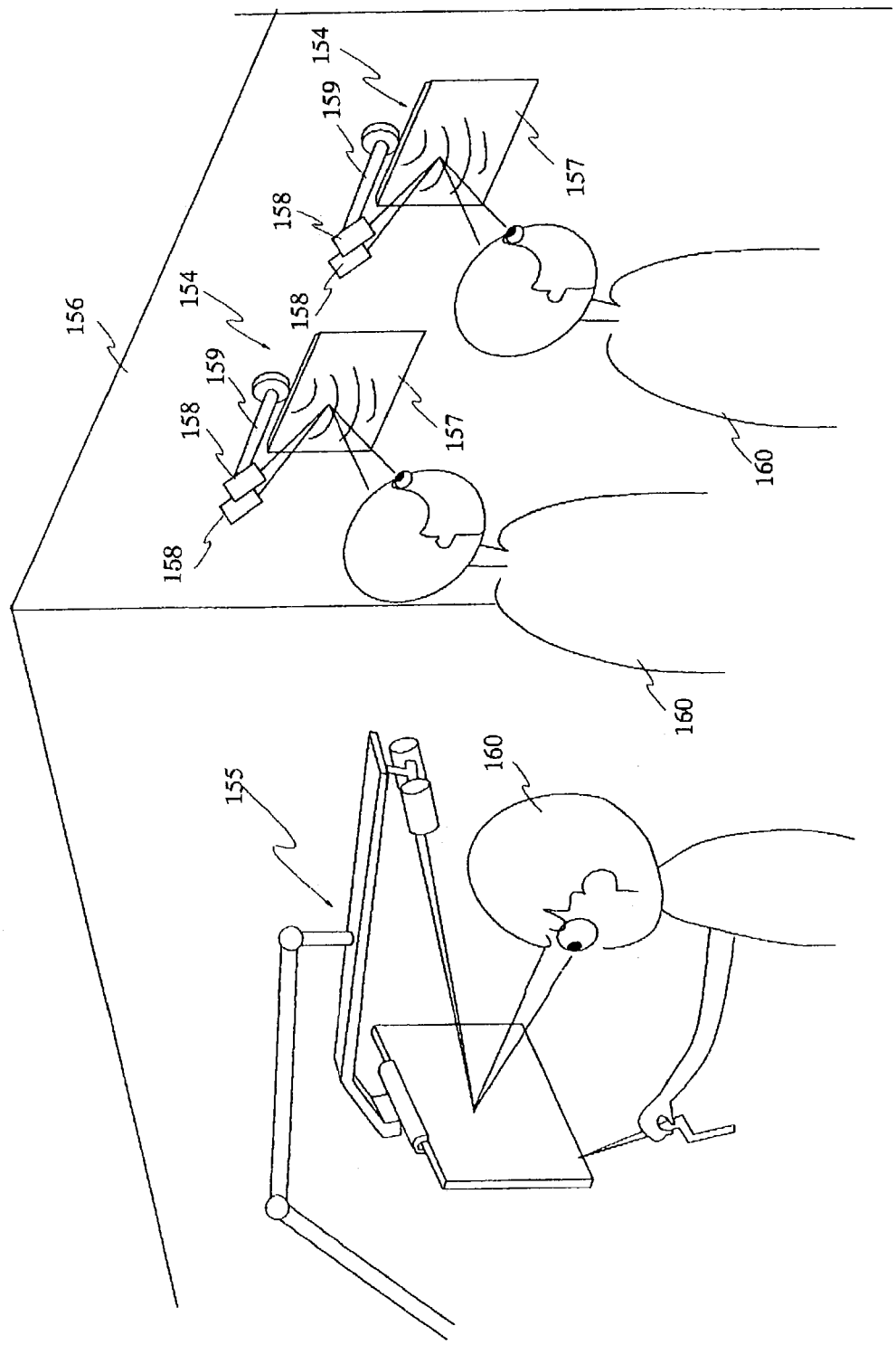
FIG. 18 illustrates an eighth preferred embodiment of a construction of the operating apparatus of the present invention.

FIG. 18 shows the structure of an operating device concerned with an eighth embodiment of the present invention.

Because the eighth embodiment is similar in structure to that of the first embodiment, only difference are explained, the same numbers are given to the same structure, and an explanation thereof is omitted.

In FIG. 18, 154 is the three-dimensional observation apparatus of this embodiment, 155 is the three-dimensional observation apparatus described with regard to the first embodiment, 156 is the wall of the operating room, 157 are image projection panels placed on the wall 156 of the operating room, 158 are image projectors, 159 are support arms which hold the image projectors 158 on the wall 156, and 160 are observers. The support arm 159 keeps the image projection panels 157 placed on the wall 156 and the image projectors 158 supported by the support arms 159 in the positional orientation of the first embodiment and it can make use of the operating room widely and effectively.

Figure 19:
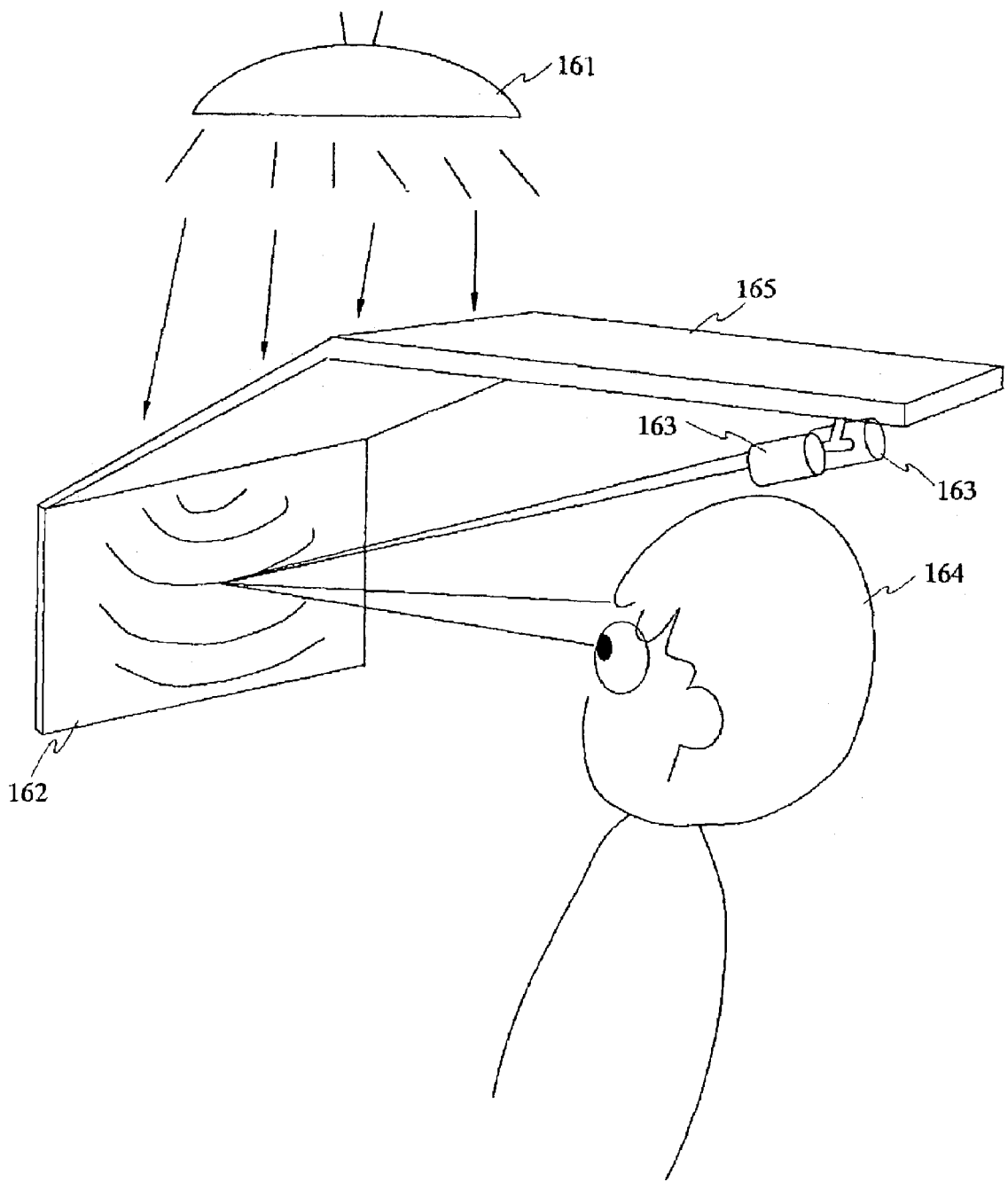
FIG. 19 illustrates a ninth preferred embodiment of a construction of the operating apparatus of the present invention.

FIG. 19 shows the structure of an operating device concerned with a ninth embodiment of the present invention.

Because the ninth embodiment is similar in structure to that of the first embodiment, only differences are explained, the same numbers are given to the same structure, and an explanation thereof is omitted.

In FIG. 19, 161 is a shadow-less fluorescent light in the operating room, 162 is an image projection panel, 163 are image projectors, 164 is an observer, 165 is the support arm which supports the image projection panel 162 and the image projectors 163. The support arm 165 has a board-shape which prevents the light from the shadow-less fluorescent light from being projected on the image projection panel 162.

According to the three-dimensional observation apparatus of the ninth embodiment, indoor lighting light such as the shadow-less fluorescent light is never projected on the image projection panel 162. Therefore, an observation image is never made to deteriorate, and a clear image can be observed.

FIG. 20 shows the structure of an operating device concerned with a tenth embodiment of the present invention.

Because the tenth embodiment is similar in structure to that of the first embodiment, only differences are explained, the same numbers are given to the same structure, and an explanation thereof is omitted.

In FIG. 20, 166 are image projectors, 167 is an image projection panel, 168 is a support arm which supports the image projectors 166 and the image projection panel 167, 169 is an attaching and detaching mechanism of the image projection panel 167. The support arm 168 supports the image projection panel 167, however, the image projection panel 167 can be removed from the support arm 167 if necessary and it can be installed again. A means for fixing the panel to the attaching and detaching mechanism, such as by a press-fit or snap-fit, or with locking screws and knobs is available.

According to this structure, when a three-dimensional observation is unnecessary, the image projection panel 167 can be quickly removed from in front of observer's eyes. Therefore, the sight of the observer is not unnecessarily obstructed.

Figure 24:
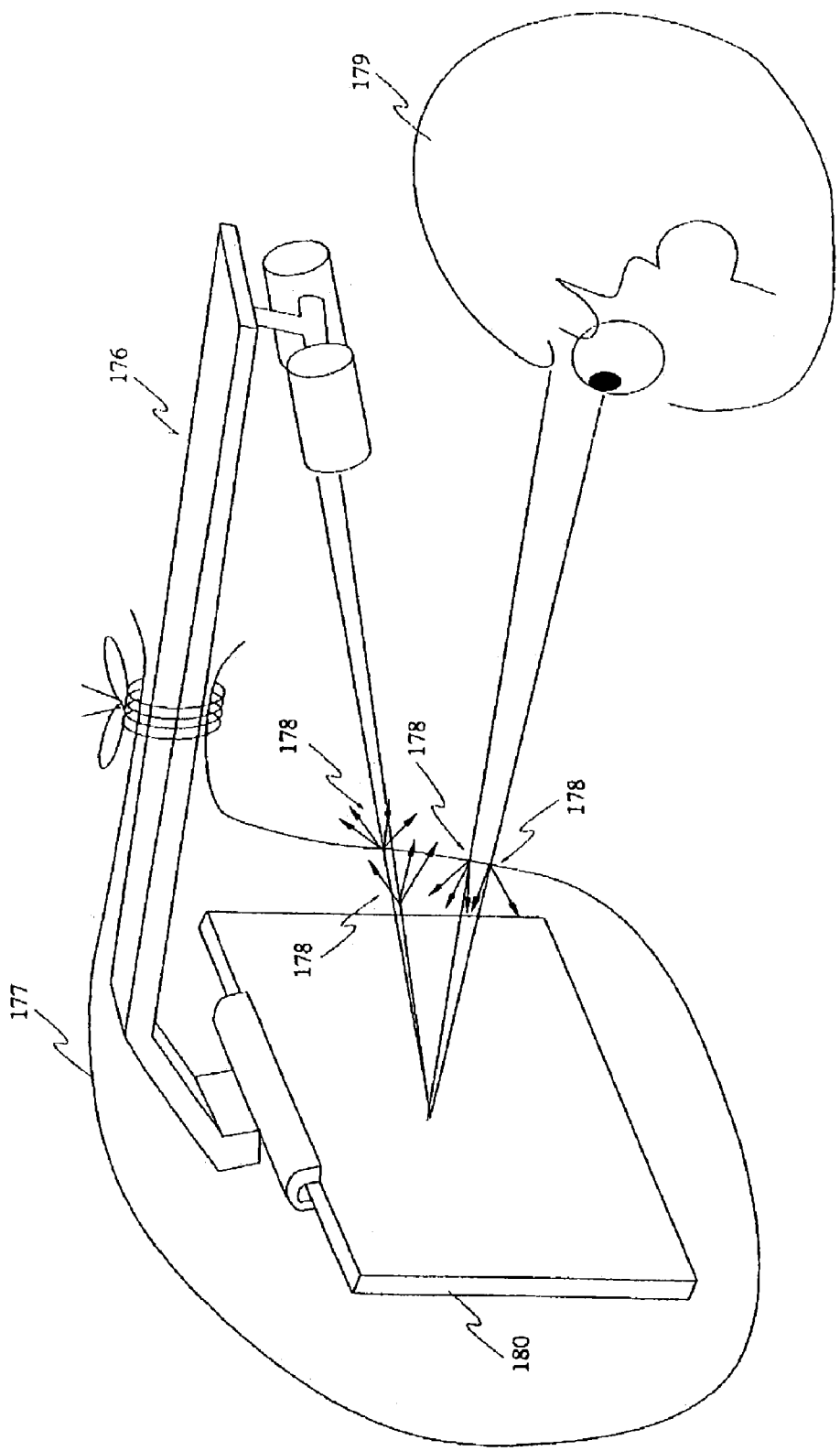
FIG. 24 is a forth illustration which explains the disposable panel of FIG. 21.

An eleventh embodiment of the present invention is shown with regard to FIG. 24.

FIG. 21 shows a disposable panel, FIG. 22 is a second figure to explain the disposable panel of FIG. 21, FIG. 23 is a third figure to explain the disposable panel of FIG. 21, and FIG. 24 is a fourth figure to explain the disposable panel of FIG. 21.

Because the eleventh embodiment is similar in structure to that of the first embodiment, only differences are explained, the same numbers are given to the same structure, and an explanation thereof is omitted.

As for the eleventh embodiment, an image projection panel 169 is a sterilized disposable panel. Preferably, the shape of the image panel 169 is the same as the image projection panel of the three-dimensional observation device explained in the first embodiment.

FIG. 21 to FIG. 23 explain the disposable panel which is sterilized. In FIG. 21 to FIG. 23, 169 is the sterilized image projection panel, 170 is a sterilized pack to keep the contents in a sterile condition, 171 is a three-dimensional observation apparatus, 172 is an opened sterilized pack, 173 is the image projection panel being used, 190 is the three-dimensional observation apparatus from which an image projection panel is removed, 174 is a trash can, and 175 is a discarded image projection panel.

FIG. 21 shows the condition of the image projection panel before use, where the image projection panel 169 sterilized in advance and disposed in a sterilized pack 170 for keeping the image projection panel 169 in a sterile condition.

FIG. 22 shows the condition of the image projection panel during use. The sterilized pack is opened and the image projection panel is taken out and the installed on the three-dimensional observation apparatus 171. Then the projection panel provides an observer with a three-dimensional observation.

FIG. 23 shows the condition of the image projection panel after use. It is removed from the three-dimensional observation apparatus 190 and thrown away.

According to this structure, it is not necessary to cover the image projection panel with sterilized drape separately to create a sterile condition when the three-dimensional observation apparatus is used in the operating room. The deterioration of the quality of the image, which occurs by a light beam penetrating the sterilized drape explained by FIG. 24, can be prevented.

FIG. 24 explains the quality of the image, 176 is a three-dimensional observation apparatus, 177 is the sterilized drape, 178 is the reflection dispersion light which occurs when a light beam penetrates a sterilized drape, 179 is an observer, and 180 is an image projection panel. The image projection panel 180 is covered with the sterilized drape 177. Reflection light and scattered light 178 occur when a light beam penetrates the sterilized drape 177. This reflection dispersion light causes deterioration in the quality of the observation image.

It will be obvious to those having skill in the art that many changes may be made in the above-described details of the preferred embodiments of this invention. The scope of this invention, therefore should be determined by the following claims.

What is claimed is:

1. A device controlled with a treatment instrument comprising:
    a system for generating an icon to which control of the device is assigned;
    an observation apparatus having a panel on which an observation image and the icon generated by the system are displayed;
    a first marker marked on the observation apparatus;
    a second marker marked on the treatment instrument;
    a position detector for detecting a position of the first marker to get a position of the icon, and for detecting a position of the second marker to get a tip position of the treatment instrument, so that an operator can control the device by touching the icon with the tip of the treatment instrument.

2. The device according to claim 1, wherein the icon is displayed as an image having no parallax even if it is viewed with the right eye or viewed with the left eye.

3. The device according to claim 1, further comprising:
    at least one image projector for projecting the observation image and the icon on the panel of the observation apparatus to display them thereon.

4. The device according to claim 1, wherein
    the panel of the observation apparatus is used in sterilized conditions.

5. The device according to claim 1, further comprising:
    an image projector for the right eye of an observer for projecting the observation image for the right eye on the panel of the observation apparatus;
    an image projector for the left eye of the observer for projecting the observation image for the left eye on the panel of the observation apparatus, wherein
    the observation image for the right eye and the observation image for the left eye have a parallax for each other, and the panel of the observation apparatus has an optical power so that the observer can observe the observation image as a three-dimensional image.

6. The device according to claim 5, wherein
    the panel of the observation apparatus has a Fresnel mirror surface.

* * * * *